United States Patent
Chu et al.

(10) Patent No.: US 8,021,869 B2
(45) Date of Patent: *Sep. 20, 2011

(54) METHOD OF CELL STORAGE IN A DELIVERY SYSTEM COMPRISING A FIBROUS MATRIX

(75) Inventors: Benjamin Chu, Setauket, NY (US); Benjamin S. Hsiao, Setauket, NY (US); Michael Hadjiargyrou, Coram, NY (US); Dufei Fang, Painted Post, NY (US); Xinhua Zong, Centereach, NY (US); Kwangsok Kim, Setauket, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 898 days.

This patent is subject to a terminal disclaimer.

(21) Appl. No.: 11/986,107

(22) Filed: Nov. 20, 2007

(65) Prior Publication Data

US 2009/0155340 A1    Jun. 18, 2009

Related U.S. Application Data

(60) Division of application No. 10/919,616, filed on Aug. 17, 2007, now Pat. No. 7,323,190, which is a continuation of application No. 09/953,114, filed on Sep. 14, 2001, now Pat. No. 6,790,455.

(51) Int. Cl.
*C12N 1/04* (2006.01)
*C12N 11/08* (2006.01)
*C12N 11/04* (2006.01)
*C12N 5/00* (2006.01)
*C12N 5/07* (2010.01)
*A61F 2/00* (2006.01)

(52) U.S. Cl. ....... 435/260; 424/426; 424/93.7; 435/180; 435/182; 435/395

(58) Field of Classification Search .................. None
See application file for complete search history.

(56) References Cited

U.S. PATENT DOCUMENTS

| | | |
|---|---|---|
| 3,975,565 A | 8/1976 | Kendall |
| 4,043,331 A | 8/1977 | Martin et al. |
| 4,323,525 A | 4/1982 | Bornat |
| 4,345,414 A | 8/1982 | Bornat et al. |
| 4,468,922 A | 9/1984 | McCrady et al. |
| 4,663,286 A | 5/1987 | Tsang et al. |
| 4,675,189 A | 6/1987 | Kent et al. |
| 4,688,387 A * | 8/1987 | Conaway ............... 435/1.3 |
| 4,689,186 A | 8/1987 | Bornat |
| 4,803,168 A | 2/1989 | Jarvis, Jr. |
| 4,810,180 A | 3/1989 | Isner |
| 4,878,908 A | 11/1989 | Martin et al. |
| 4,911,867 A | 3/1990 | Burlet et al. |
| 5,066,755 A | 11/1991 | Lemstra |
| 5,116,747 A | 5/1992 | Moo-Young et al. |
| 5,266,480 A * | 11/1993 | Naughton et al. ........... 435/371 |
| 5,296,172 A | 3/1994 | Davis et al. |
| 5,567,612 A | 10/1996 | Vacanti et al. |
| 5,569,528 A | 10/1996 | Van der Loo et al. |
| 5,763,267 A * | 6/1998 | Kurjan et al. ............. 435/293.1 |
| 5,783,111 A | 7/1998 | Ikkala et al. |
| 6,013,371 A | 1/2000 | Hager et al. |
| 6,031,148 A | 2/2000 | Hayes et al. |
| 6,090,910 A | 7/2000 | Shinoda et al. |
| 6,106,913 A | 8/2000 | Scardino et al. |
| 6,143,293 A * | 11/2000 | Weiss et al. ................. 424/93.7 |
| 6,171,610 B1 | 1/2001 | Vacanti et al. |
| 6,177,095 B1 | 1/2001 | Sawhney et al. |
| 6,206,914 B1 | 3/2001 | Soykan et al. |
| 6,218,441 B1 | 4/2001 | Meluch et al. |
| 6,231,881 B1 | 5/2001 | Usala et al. |
| 6,238,705 B1 | 5/2001 | Liu et al. |
| 6,685,956 B2 | 2/2004 | Chu et al. |
| 6,689,374 B2 | 2/2004 | Chu et al. |
| 6,753,454 B1 * | 6/2004 | Smith et al. .................. 602/41 |
| 6,790,455 B2 | 9/2004 | Chu et al. |
| 7,172,765 B2 | 2/2007 | Chu et al. |

FOREIGN PATENT DOCUMENTS

| | | |
|---|---|---|
| WO | WO 98/03267 | 1/1988 |
| WO | WO 01/26610 A1 | 4/2001 |
| WO | WO 01/27365 A1 | 4/2001 |

OTHER PUBLICATIONS

Bezwada et al., "Poly(p-Dioxanone) and Its Copolymers," *Handbook of Biodegradable Polymers*, # 29-61 (1997).
Dzenis et al., "Polymer Hybrid Nano/Micro Composites," *Proceedings of the American Society for Composites—Ninth Technical Conference*, pp. 657-665 (1994).

* cited by examiner

*Primary Examiner* — David Naff
(74) *Attorney, Agent, or Firm* — Hoffmann & Baron, LLP

(57) ABSTRACT

Cell storage and delivery systems and methods for storing and delivering viable cells to a mammal are disclosed. The cell storage and delivery systems include a biodegradable and/or bioabsorbable fibrous matrix physically associated with viable cells to contain and release the cells at a controlled rate. The biodegradable and/or bioabsorbable matrix can be formed by electrospinning fibers of biodegradable and/or bioabsorbable fiberizable material. The methods include methods for storing viable cells and for delivering viable cells to a mammal using the cell storage and delivery system.

22 Claims, 12 Drawing Sheets

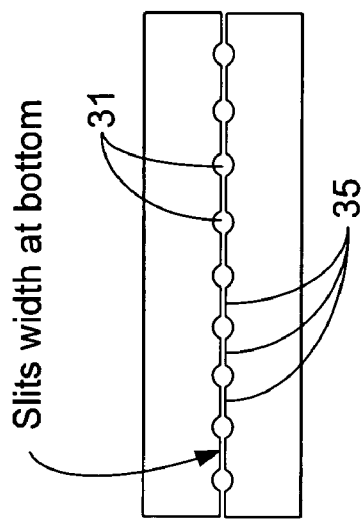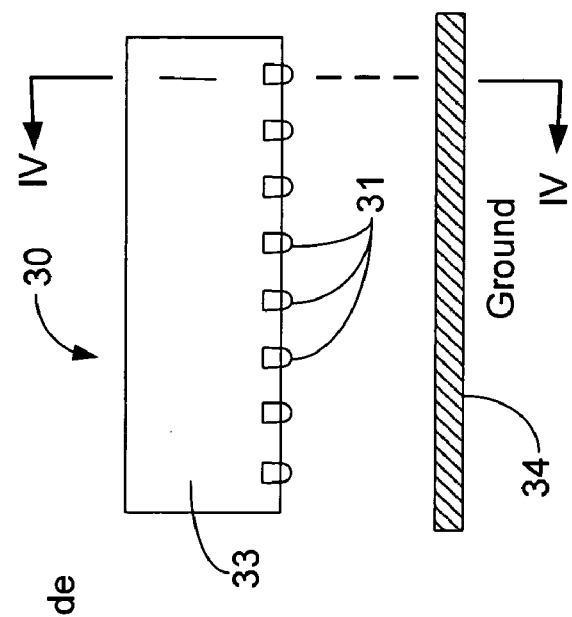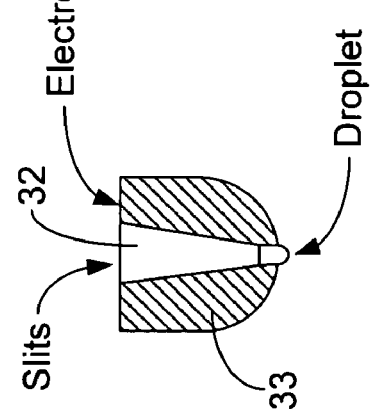

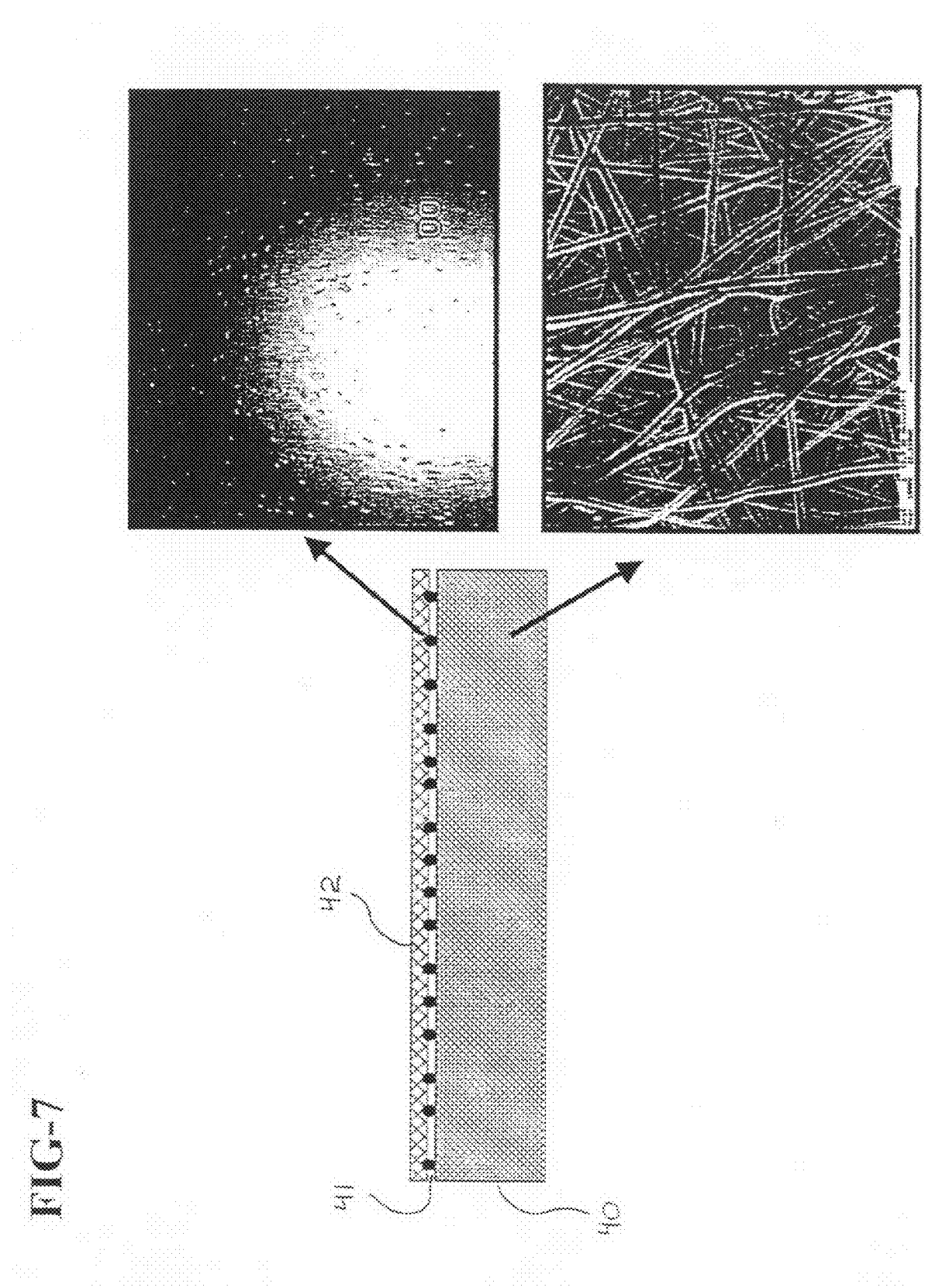

FIG-11 Electrospun membrane before and after quenching in liquid nitrogen.

Optical micrograph of cells released from frozen membrane in 3 days.

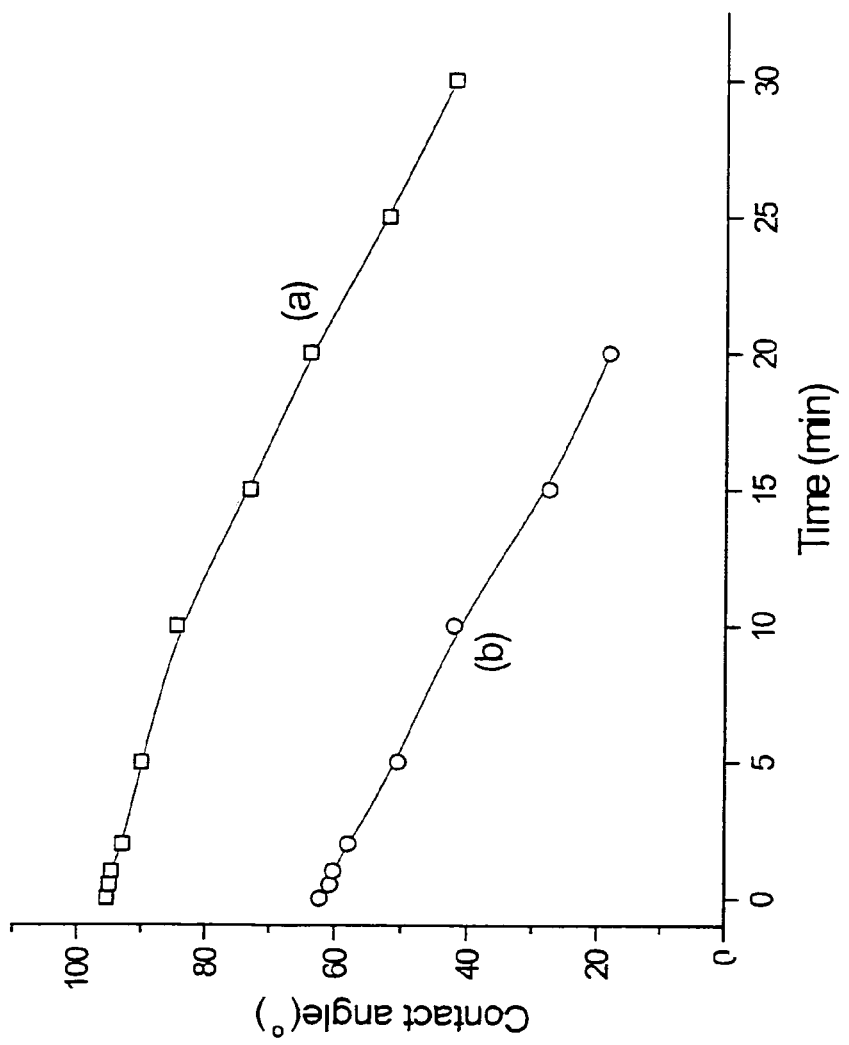
FIG-13  Contact angle change of electrospun PLGA90/lactide 10 blend; (a) without dipping, (b) with dipping process.

METHOD OF CELL STORAGE IN A DELIVERY SYSTEM COMPRISING A FIBROUS MATRIX

This application is a divisional application of U.S. application Ser. No. 10/919,616, filed on Aug. 17, 2004, now U.S. Pat. No. 7,323,190, issued on Jan. 29, 2008, which is a continuation of application Ser. No. 09/953,114, filed on Sep. 14, 2001, now U.S. Pat. No. 6,790,455, issued on Sep. 14, 2004, both of which are incorporated herein by reference in their entirety.

BACKGROUND OF INVENTION

The present invention relates to cell storage and delivery systems. More specifically, the present invention is directed to biodegradable and/or bioabsorbable fibrous articles having utility as a carrier for viable cells.

Methods and compositions for encapsulating core materials, e.g., materials containing drugs, have been disclosed. These methods generally involve encapsulating the core material within a microcapsule by forming a semipermeable membrane around the core material.

Although a number of processes for microencapsulation of core material have been developed, most of these processes cannot be used for pH, temperature or ionic strength-sensitive material such as viable cells because of the harsh conditions necessary for encapsulation. U.S. Pat. No. 4,352,883 to Lim discloses what is believed to be one of the first processes for successfully encapsulating viable tissue or cells within a semipermeable membrane. In the process, a temporary capsule of a gellable material, e.g., an anionic gum such as sodium alginate, is formed about the tissue or cells and a permanent, semipermeable membrane is formed by cross-linking surface layers of the temporary capsule. Specifically, a mixture of the gum and the core material is subjected to a gelling solution, preferably a calcium ion solution, to produce a temporary capsule. The resulting temporary capsule is reacted with a solution of a polycationic material to form a permanent membrane. The interior of the capsule may be reliquified by reestablishing conditions under which the anionic gum is liquid, e.g., changing the ionic environment by placing the capsules in phosphate buffered saline. Reliquification of the interior of the capsule facilitates nutrient transport across the membrane, promoting cell growth. The process need not damage the core material or hamper the viability of cells because the temperature, ionic strength, and pH ranges used in the encapsulation process need not be harsh.

A preferred embodiment of the Lim encapsulation technique involves the formation of shape-retaining gelled masses that contain the material to be encapsulated, followed by deposition of a membrane on the surface of the gelled masses. The membrane is formed as relatively high molecular weight materials contact the gel masses and form ionic cross-links with the gel. Lim discloses that lower molecular weight cross-linking polymers permeate further into the structure of the gelled masses and result in a reduction of pore size. Lim also discloses that the duration of membrane formation affects pore size. Given a pair of reactants, the longer the cross-linking polymer solution is exposed to the gelled mass, the thicker and less permeable the membrane.

While the techniques for porosity control and membrane formation disclosed in the Lim patent may form acceptable membranes, they do not allow fine tuning of the membrane porosity, but rather set rough differential filtering limits.

In addition to improved porosity, for commercial purposes it is also important to be able to consistently produce microcapsules in large numbers having defect-free membranes. In this regard, membranes formed by the Lim techniques occasionally have protruding portions of cells or have cells anchored on the capsules. The Lim techniques also may produce capsules containing voids that allow cells, the substance of interest, or unwanted contaminants to escape from the capsule. If a small fraction of the microcapsules made with a specific purpose in mind have membrane voids, many of the objectives and advantages of the processes would be frustrated. Accordingly, encapsulation processes that promote membrane uniformity and avoid random membrane defects are advantageous to commercial practice.

Other methods for encapsulating or otherwise immobilizing biologically active materials, e.g. viable cells, have been disclosed which involve suspending the biologically active material in a gel composition and incorporating the gel material into the pores of a semi-permeable or permeable structure, or reacting the gel material to form a porous polymeric coating over the gel material. For example, U.S. Pat. No. 5,116,747 to Moo-Young et al. describes the immobilization of cells and other biologically active materials within a semipermeable membrane or microcapsule composed of an anionic polymer such as alginate induced to gel in the presence of calcium and/or a polymeric polycation such as chitosan.

U.S. Pat. No. 4,663,286 to Tsang et al. describes the encapsulation of solid core materials such as cells within a semipermeable membrane, by suspending the core material in a solution of a water-soluble polyanionic polymer, preferably alginate salts, forming droplets, and gelling the polyanion with a polyvalent polycation such as a polypeptide, a protein or a polyaminated polysaccharide, preferably polylysine, polyarginine, or polyornithine. This patent further teaches controlling the porosity and permeability of the disclosed compositions to molecules ranging from about 60,000 to about 900,000 Daltons by changing the degree of hydration of the polymer. Incubation in saline or chelating agents increases hydration and expands the gels, whereas incubation in calcium chloride contracts the gel mass. Increases in charge density of the polycationic membrane generally produces smaller pores. Increases in the molecular weight of the polycationic polymer generally produces a thicker, less permeable membrane.

U.S. Pat. No. 4,803,168 to Jarvis describes the encapsulation of core materials such as cells, enzymes, antibodies, hormones, etc. within a semipermeable membrane or microcapsule composed of an aminated polymeric inner layer such as chitosan ionically bound to an anionic polymeric outer layer such as polyglutamic or polyaspartic acid.

While these other methods may provide a generally useful means for encapsulating cells, techniques involving the formation of a membrane around a gel core material containing the cells can have certain drawbacks. As discussed above, it is difficult to fine tune the membrane porosity and to form defect free membranes. Moreover, there can be drawbacks in trying to store cells using such materials. Viable cells are typically stored by freezing, for example, in liquid nitrogen. However, the gel core materials and polymeric coating can become brittle and difficult to handle when inserted in a liquid nitrogen environment. Thus, it would be commercially advantageous to provide membranes having controlled porosity and physical integrity which are useful for containing viable cells and which exhibit excellent mechanical handling ability even when frozen, e.g. in liquid nitrogen. It would also be advantageous to provide a system for containing viable cells which can be formed around the cells under mild conditions without the need for a gel core material carrier for the cells.

Polymeric membranes produced by an electrospinning technique have been suggested as being useful for biological membranes such as substrates for immobilized enzymes and catalyst systems, wound dressing materials and artificial blood vessels, as well as for aerosol filters and ballistic garments.

Electrospinning is an atomization process of a conducting fluid that exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. Although membranes can be produced by electrospinning under mild conditions, no practical industrial process has been implemented for producing membranes useful for medical applications. This is because with the production of small fibers, such as nanosize fibers, the total yield of the process is very low and a scale-up process, which maintains the performance characteristics of the films (or membranes), cannot be easily achieved.

Thus, there is a need for improved cell storage and delivery systems which can be produced on an industrial scale, which do not have the above-mentioned disadvantages.

SUMMARY OF INVENTION

According to the present invention, it has now been found that viable cells can be stored and later delivered to a mammal with a delivery system that contains a biodegradable and/or bioabsorbable matrix which avoids the above-mentioned disadvantages.

In one aspect, the invention relates to a cell delivery system which includes a biodegradable and/or bioabsorbable fibrous matrix and viable cells physically associated with the matrix as a carrier whereby the cells are contained and released at a controlled rate.

Preferably, the biodegradable and/or bioabsorbable fibrous matrix is formed by electrospinning fibers of biodegradable and/or bioabsorbable fiberizable material.

Preferably, the matrix will contain electrospun fibers having fiber diameters in the range from about 10 up to 1,000 nanometers, more preferably, in the range from about 20 to about 500 nanometers.

In one embodiment, the matrix contains a composite of different biodegradable and/or bioabsorbable fibers.

In another embodiment, the matrix contains an asymmetric composite of different biodegradable and/or bioabsorbable fibers.

Different fibers can include fibers of different diameters, fibers of different biodegradable and/or bioabsorbable materials, or fibers of both different diameters and different biodegradable and/or bioabsorbable materials.

Preferably, the matrix will contain at least about 20 weight percent of submicron diameter fibers, more preferably, at least about 50 weight percent of submicron diameter fibers.

The biodegradable and/or bioabsorbable fiberizable material is preferably a biodegradable and/or bioabsorbable polymer. The biodegradable and/or bioabsorbable polymer preferably contains a monomer selected from the group consisting of a glycolide, lactide, dioxanone, caprolactone, trimethylene carbonate, ethylene glycol and lysine.

In one embodiment, the biodegradable and/or bioabsorbable polymer is a biodegradable and/or bioabsorbable linear aliphatic polyester, preferably a polyglycolide or a copolymer poly(glycolide-co-lactide).

The biodegradable and/or bioabsorbable fiberizable material can also include a material derived from biological tissue, e.g., collagen, gelatin, polypeptides, proteins, hyaluronic acid and derivatives or synthetic biopolymers.

The fibers of different biodegradable and/or bioabsorbable materials can include fibers having different chemical composition, such as different polymeric materials, different molecular weights of the same polymeric material, different blends of polymers, materials having different additives or materials having different concentration of additives.

In another embodiment the matrix will contain different fibers, i.e. different diameters and/or different materials, having diameters in the range from a few nanometers up to almost about one micron, more preferably about 10 up to about 1000 nanometers and most preferably from about 20 to about 500 nanometers. The fibers of different diameters can include both fibers having diameters less than 300 nanometers and fibers having diameters greater than 300 nanometers.

In yet another embodiment, the fibrous matrix is formed by electrospinning different fibers of different materials, in which the article contains a composite of different fibers. Preferably, the composite of different fibers will contain submicron diameter fibers. The composite can be an asymmetric composite.

The matrix can also contain small blobs of biodegradable and/or bioabsorbable material. Preferably, the small blobs will have diameters in the range of about 20 to about 500 nanometers and, more preferably, about 200 to about 1500 nanometers.

In one embodiment, the article also contains at least one cell culture additive (as defined below). Examples of cell culture additives include additives which effect cell-membrane affinity, such as peptides, proteins, hyaluronic acid, as well as hydrophilic monomers, oligomers or polymers. The additive can be contained at the surface and/or within the biodegradable and/or bioabsorbable material itself, including within the fibers or within the small blobs of material, if present. In such a case, the fibers (and/or small blobs) can contain different concentrations of the additives or different additives.

The matrix can also have the structure of a plurality of layers, wherein at least one of the layers is a composite (or asymmetric composite) of different biodegradable and/or bioabsorbable fibers. In such a case, the article can also contain at least one additive between at least two of the layers.

Preferably, the cell delivery system is formed by electrospinning fibers of biodegradable and/or bioabsorbable fiberizable material in a layered structure, which includes:

a relatively thick base layer of a biodegradable and/or bioabsorbable fibrous matrix, a dispersion of viable cells dispersed over the surface of the base layer, a relatively thin top layer of a biodegradable and/or bioabsorbable fibrous matrix covering the dispersion of cells and adhered to the surface of the base layer, wherein the top layer has sufficient porosity to allow transfer of $O_2$ and nutrients from outside the top layer to the cells and transfer of $CO_2$ from the cells to the outside of the top layer, and an optional porous partition layer to separate the sandwich layers.

The base layer preferably has a thickness in the range of about 20 to about 500 microns and, more preferably, about 50 to about 250 microns.

The top layer preferably has a thickness in the range of about 1 to about 50 microns and, more preferably, about 5 to about 20 microns.

The optional partition (or spacer) layer preferably comprises a biodegradable and/or bioabsorbable material having a relatively fast adsorption rate. Examples of such materials are the same as those made up of the bottom layer but with a different composition and morphology so as to have larger (bicontinuous) pores of sizes ranging from 1 to 5 microns and with a faster degradation rate in order to keep the embedded cells alive. The partition layer preferably has a thickness of about 1 to about 200 microns and, more preferably, about 5 to about 100 microns. It should have the ability for fast replacement by fluids that contain nutrients and oxygen for the cells and that can remove carbon dioxide and wastes. In one embodiment the thin top layer and the optional spacer layer can be integrated into one single layer that performs these functions.

The cell delivery system is preferably capable of being frozen and returned to room temperature without adversely affecting the integrity of the fibrous matrix (or layers) or the viability of the cells.

The cell delivery system can be used in connection with a variety of tissue precursor cells including differentiated cells obtained (e.g., harvested) from tissue of the lung, liver, kidney, thymus, thyroid, heart, brain, pancreas, bone, and the like. Tissue precursor cells can also include cells which are pre-selected to differentiate into specific cell types or so-called "stem" cells (or "progenitor" cells) that are undifferentiated precursor cells.

The tissue precursor cells can include any of the following: epidermal cells, chondrocytes and other cells that form cartilage, macrophages, dermal cells, muscle cells, hair follicles, fibroblasts, organ cells, osteoblasts and other cells that form bone, endothelial cells, mucosal cells, pleural cells, ear canal cells, tympanic membrane cells, peritoneal cells, Schwann cells, corneal epithelial cells, gingiva cells, neural cells, neural stem cells such as central nervous system (CNS) stem cells, e.g., spinal cord or brain stem cells, as well as autonomic nervous system (ANS) stem cells, e.g., post-ganglionic stem cells from the small intestine, bladder, liver, lung, and heart, (for engineering sympathetic or parasympathetic nerves and ganglia), tracheal epithelial cells, hepatocytes, pancreatic cells, and cardiac cells. The tissue precursor cells can also be neuroendocrine stem cells.

In another aspect, the cell delivery system can be used with isolated, mammalian adult autonomic nervous system neural stem cells. These stem cells can be isolated from any innervated tissues in the body, including the heart, bladder, intestine, lung, liver, and kidney tissue. The invention also includes isolated, mammalian neuroendocrine stem cells, e.g., adult cells, such as those isolated from the pancreas (adult or fetal), or adult cells isolated from the adrenal medulla.

The cell delivery system can contain a supply of nutrients for the cells. Examples of nutrients include sugars, amino acids, growth factors, vitamins, hormones, cytokines, etc. The nutrients can be contained between the layers and/or within the fibers.

In another aspect, the invention is directed to a method for storage of living cells for delivery to a mammal. The method includes:

(a) providing a cell delivery system which contains:
(i) viable cells; and
(ii) a biodegradable and/or bioabsorbable fibrous matrix as a carrier physically associated with the cells to contain and release the cells at a controlled rate;

(b) cooling the cell delivery system down to a preservation temperature under conditions which maintain the integrity of the system; and (c) maintaining the cell delivery system at or below the preservation temperature until a time when cell delivery is desired.

The preservation temperature is preferably below at least about −50° C. and the cooling step is preferably carried out by submerging the cell delivery system in liquid nitrogen.

In yet another aspect, the invention is directed to a method for delivery of viable cells to a mammal. The method includes:

(a) providing a cell delivery system containing:
(i) viable cells; and
(ii) a biodegradable and/or bioabsorbable fibrous matrix as a carrier physically associated with the cells to contain and release the cells at a controlled rate; and (b) positioning the cell delivery system at a desired location for cell delivery to the mammal.

The invention can also be used as a method for delivering viable cells in the treatment of defective tissue. For example, it can be used for treating defective nervous tissue by locating the physical boundaries of the defective tissue; removing the defective tissue to create a cavity and exposing healthy nervous tissue at the surfaces of the cavity; loading a neural stem cell composition into a cell delivery system in the general size and shape of the cavity, wherein the neural stem cells are selected to differentiate into the healthy nervous tissue; and implanting the delivery system into the cavity, thereby treating the defective nervous tissue. The defective nervous tissue can be CNS tissue, e.g., in the brain or spinal cord, ANS tissue, or neuroendocrine tissue. The neural stem cells can be isolated from the healthy nervous tissue. In this method, a spacer can be implanted into the cavity temporarily, and then replaced with the cell delivery system.

The present invention provides cell delivery and storage systems containing a biodegradable and/or bioabsorbable fibrous matrix and having improved performance and handling characteristics, including improved performance in both cell storage and cell delivery.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE FIGURES

FIG. 4(a) is a side view schematic of a multiple spinneret system for producing membranes in accordance with the invention.

FIG. 4(b) is a cross-sectional view of the spinneret system of FIG. 4(a) as seen along viewing lines IV-IV thereof.

FIG. 4(c) is a bottom view of the multiple spinneret system of FIG. 4(a).

FIG. 7 is a schematic of a cell delivery system produced in Example 1.

FIG. 13 is a graph showing the contact angle as a function of the time for a cell solution on the surface of the membranes as described in Example 5.

DETAILED DESCRIPTION OF THE INVENTION

Figure 1:
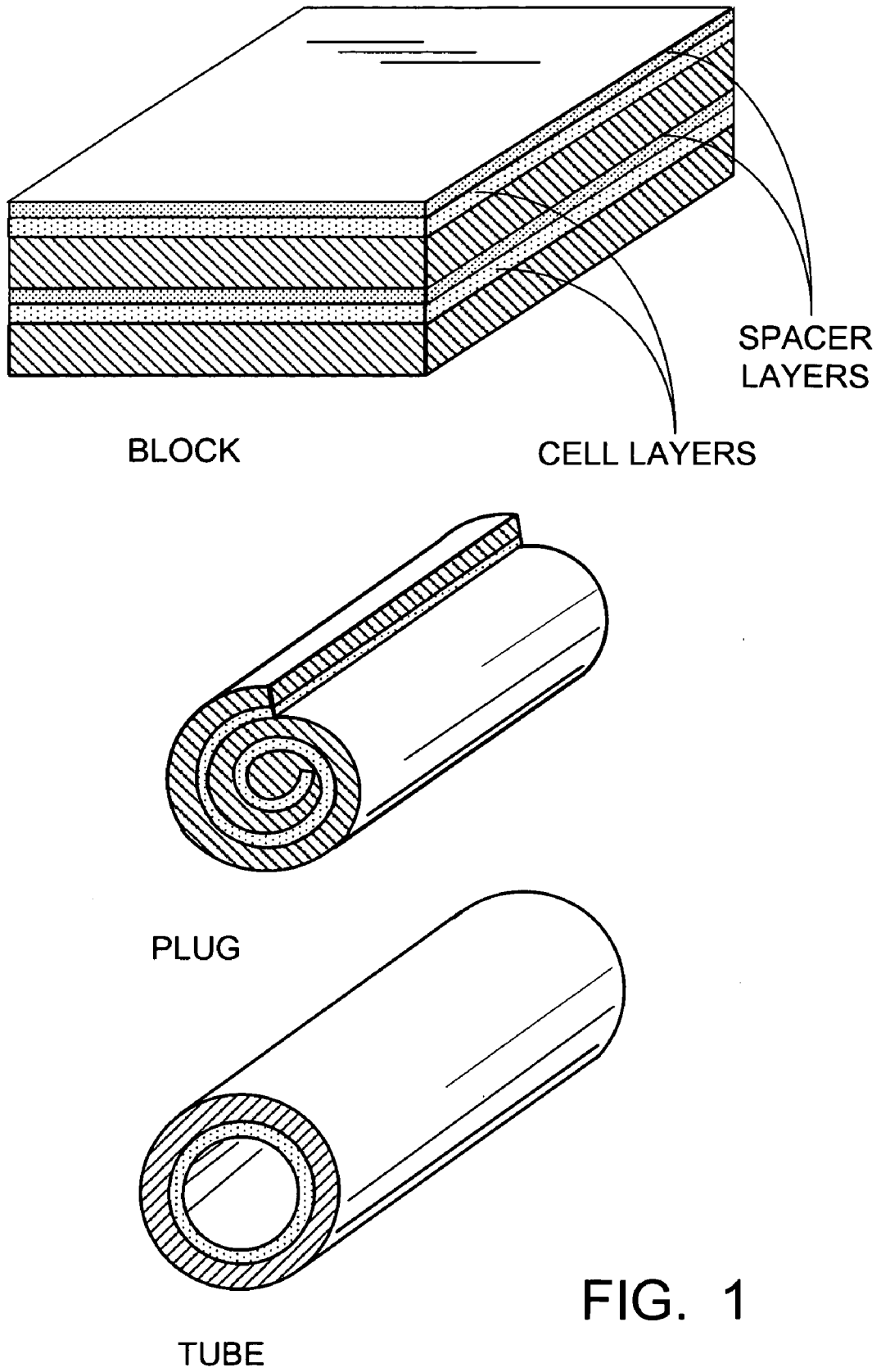
FIG. 1 is a schematic of a cell delivery system containing a sandwiched PLA/cell/HA membrane formed into three dimensional shapes.

The present invention is directed to a cell delivery system which includes a biodegradable and/or bioabsorbable fibrous matrix and methods for using the cell delivery system for storing viable cells and later delivering the cells to a mammal.

In one aspect, the invention relates to a cell delivery system which includes a biodegradable and bioabsorbable fibrous matrix and viable cells physically associated with the matrix as a carrier whereby the cells are contained and released at a controlled rate.

Preferably, the fibrous matrix is formed by electrospinning fibers of biodegradable and/or bioabsorbable fiberizable material.

In one embodiment, the fibrous matrix contains a composite of different biodegradable and/or bioabsorbable fibers.

In another embodiment, the fibrous matrix contains an asymmetric composite of different biodegradable and/or bioabsorbable fibers.

In yet another embodiment, the fibrous matrix also includes fibers and/or hydrogels of at least one non-biodegradable/non-bioabsorbable material.

By the term biodegradable is intended a material which is broken down (usually gradually) by the body of an animal, e.g. a mammal, after implantation.

By the term bioabsorbable is intended a material which is absorbed or resorbed by the body of an animal, e.g. a mammal, after implantation, such that the material eventually becomes essentially non-detectable at the site of implantation.

By the terminology "biodegradable and/or bioabsorbable fiberizable material" is intended any material which is biocompatible, as well as biodegradable and/or bioabsorbable, and capable of being formed into fibers, as described more fully below. The material is also capable of being formed into a fibrous article which is suitable for implantation into an animal and capable of being biodegraded and/or bioabsorbed by the animal.

The biodegradable and/or bioabsorbable fiberizable material is preferably a biodegradable and bioabsorbable polymer. Examples of suitable polymers can be found in Bezwada, Rao S. et al. (1997) *Poly(p-Dioxanone) and its copolymers, in Handbook of Biodegradable Polymers*, A. J. Domb, J. Kost and D. M. Wiseman, editors, Hardwood Academic Publishers, The Netherlands, pp. 29-61, the disclosure of which is incorporated herein by reference in its entirety.

In a preferred embodiment the biodegradable and/or bioabsorbable polymer contains a monomer selected from the group consisting of a glycolide, lactide, dioxanone, caprolactone, trimethylene carbonate, ethylene glycol and lysine. By the terminology "contains a monomer" is intended a polymer which is produced from the specified monomer(s) or contains the specified monomeric unit(s). The polymer can be a homopolymer, random or block co-polymer or hetero-polymer containing any combination of these monomers. The material can be a random copolymer, block copolymer or blend of monomers, homopolymers, copolymers, and/or heteropolymers that contains these monomers.

In one embodiment, the biodegradable and/or bioabsorbable polymer contains bioabsorbable and biodegradable linear aliphatic polyesters such as polyglycolide (PGA) and its random copolymer poly(glycolide-co-lactide) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidney. These polymers are very different from cellulose based materials, which cannot be absorbed by the body.

These materials are also effective drug carriers for pharmaceutical products, as they meet several drug release criteria including a biocompatible and biodegradable polymer matrix that provides efficient drug loading. The degradation rate of these materials, as well as the release rate of entrapped drugs, can only be roughly controlled by varying the molecular structure and the molecular weight as there is no linear relationship between the physical properties of the constituent homopolymers or their copolymers. However, by controlling the filament diameter (to nanometer sizes) and the assembly morphology as described more fully below, the degradation rate and the drug release rate can be finely tuned. For example, Dunne et al. examined the influence of processing conditions, particle characteristics and media temperature on the degradation of PGA-co-PLA spherical particles. They found that a linear relationship between the degradation rate and particle size existed, with the larger particles degrading fastest.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran, polyamino acids, polylysine and copolymers of these materials. Any combination, copolymer, polymer or blend thereof of the above examples is contemplated for use according to the present invention. Such bioabsorbable materials may be prepared by known methods.

Particularly useful biodegradable and/or bioabsorbable polymers include poly-lactides, poly-glycolides, polycarprolactone, polydioxane and their random and block copolymers. Examples of specific polymers include poly D,L-lactide, polylactide-co-glycolide (85:15) and polylactide-co-glycolide (75:25).

Preferably, the biodegradable and/or bioabsorbable polymers used in the fibrous matrix of the present invention will have a molecular weight in the range of about 1,000 to about 8,000,000 g/mole, more preferably about 4,000 to about 250,000 g/mole.

By the terminology "composite of different biodegradable and/or bioabsorbable fibers" is intended any combination of the different fibers interleaved with each other in the form of a fibrous matrix, which can be in the form of a membrane or other three dimensional form of tailored geometry, such as a tube, rod or plug.

By the terminology "asymmetric composite of different biodegradable and/or bioabsorbable fibers" is intended a composite of different biodegradable and/or bioabsorbable fibers, having at least one of non-homogeneous porosity, assembled morphology, or variations in the ratio of different fibers, progressing through different regions of the composite material. For example, with reference to a membrane containing an asymmetric composite of different biodegradable and/or bioabsorbable fibers, the porosity, morphology or variations in fibers can be varied either in a direction perpendicular to or parallel with the surface of the membrane. Thus, an asymmetric composite of different biodegradable and/or bioabsorbable fibers can have 100 percent submicron diameter fibers on a first side of the membrane, zero percent submicron diameter fibers on the opposite side, and a progressively lower percentage of submicron diameter fibers in the direction from the first side across the thickness of the membrane.

By the terminology "different biodegradable and/or bioabsorbable fibers" is intended to include fibers of different diameters, fibers of different biodegradable and/or bioabsorbable materials, or fibers of both different diameters and different biodegradable and/or bioabsorbable materials.

By the terminology "fibers of different diameters" is intended that the article will include fibers having at least two different target (or intended) diameters.

By the terminology "fibers of different biodegradable and/or bioabsorbable materials" is intended to include fibers having different chemical composition, in the form of, for example, different polymeric materials, different molecular weights of the same polymeric material, or different additives (or concentration of additives), such as medicinal agents, peptides, proteins, hyaluronic acid, and hydrophilic monomers, oligomers or polymers.

In one embodiment, the fibrous matrix will contain different fibers having diameters in the range from a few up to about 1,000 nanometers, more preferably about 10 up to about 1000 nanometers and most preferably about 20 to about 500 nanometers.

The fibrous matrix can contain fibers having different diameters with a controlled percentage of sub-micron diameter fibers. Preferably, the article will contain at least about 10 wt % of sub-micron diameter fibers, more preferably at least about 20 wt %, and most preferably at least about 50 wt %.

In a preferred embodiment, the fibrous matrix is formed by electrospinning a plurality of layers, wherein each layer can have the same or different composition, porosity and/or morphology. At least one of the layers can be a composite (or asymmetric composite) of different biodegradable and/or bioabsorbable fibers, as discussed above. For example, a cell delivery system can be constructed by electrospinning a first membrane, depositing viable cells on the surface of the membrane, e.g., coating the surface of the membrane with a composition (e.g., solution) containing the viable cells, and then electrospinning (or depositing) a second porous membrane onto the surface of the first membrane which contains the cells.

Preferably, the cell delivery system is formed by electrospinning fibers of biodegradable and/or bioabsorbable fiberizable material in a layered structure, in which the layered structure includes:

a relatively thick base layer of a biodegradable and/or bioasorbable fibrous matrix;
   a dispersion of cells dispersed over the surface of the base layer;
   a relatively thin top layer of a biodegradable and/or bioabsorbable fibrous matrix covering the dispersion of cells and adhered to the surface of the base layer; and
   an optional porous temporary spacer for nutrients to reach the cells.

In such a structure, the base layer provides support for good handling characteristics and the top layer provides containment for the cells and has sufficient porosity to allow transfer of $O_2$ and nutrients from outside of the top layer to the cells and transfer of $CO_2$ from the cells to the outside of the top layer. The thickness, the material composition and the porosity of the top layer can be controlled by processing parameters of the electrospinning so that suitable degradation time can be obtained for the cell release.

The optional partition (or spacer) layer is used in connection with cell delivery systems having a three dimensional configuration, i.e., systems which include successive layers of viable cells, such as, for example, the layered structure (described above) rolled into a plug shaped structure. The partition layer(s) is/are positioned between the successive layers in a manner that allows fast replacement by fluids capable of providing nutrients and oxygen to the cells and removing carbon dioxide and wastes from the cells.

The partition layer preferably includes a biodegradable and/or bioabsorbable material having a relatively fast adsorption rate and a relatively large average pore size. Examples of such materials are the same as those made up of the bottom layer but with a different composition and morphology so as to have larger (bicontinuous) pores of sizes ranging from 1 to 5 microns and with a faster degradation rate in order to keep the embedded cells alive.

In one embodiment, the thin top layer and the optional partition layer can be integrated into one single layer which performs the functions of these individual layers.

The base layer will preferably have a thickness in the range of about 20 to about 500 microns, more preferably about 50 to about 250 microns, and most preferably about 100 to about 200 microns.

The top layer will preferably have a thickness in the range of about 1 to about 50 microns, more preferably about 5 to about 20 microns, and most preferably about 5 to about 15 microns.

The partition layer will preferably have a thickness of about 1 to about 200 microns, more preferably about 5 to about 100 microns, and most preferably about 10 to about 50 microns.

In another embodiment, the cell delivery system is formed by electrospinning a relatively thick base layer of a biodegradable and/or bioabsorbable fibrous matrix, distributing a dispersion of cells on the surface of the base layer and then coating a thin layer (e.g., 10 μm) of a biological gel (such as hyaluronic acid (HA), a natural product with a fast degradation rate and good cell compatibility) over the cells to entrap the cells. This approach is desirable for fast cell release.

The success of the system for cell delivery depends on the combined performance of biodegradation in the matrix, ready access of nutrients by the embedded cells and their controlled release rate. These effects should be designed and controlled independently but evaluated together.

The cell delivery system can be used in connection with a variety of tissue precursor cells including cells derived (e.g., harvested) from tissue of the lung, liver, kidney, thymus, thyroid, heart, brain, pancreas, bone, and the like. Tissue precursor cells can also include cells selected to differentiate into specific cell types or so-called "stem" cells (or "progenitor" cells) that are undifferentiated precursor cells. By the terminology "tissue precursor cells" is intended cells that are capable of forming new tissue. Examples of such cells include mesenchymal as well as stromal and neural crest cells.

Tissue precursor cells can be obtained directly from a mammalian donor, e.g., a patient's own cells; from a culture of cells from a donor; from bone marrow, embryos, placentas or umbilical cords; or from established cell culture lines. The mammal can be a mouse, rat, rabbit, guinea pig, hamster, cow, pig, horse, goat, sheep, dog, cat, and the mammal can be a human. Cells of the same species and preferably of the same immunological profile can be obtained by biopsy, either from the patient or a close relative. In the case of neural stem cells isolated from nervous tissue, they can be isolated from healthy tissue adjacent defective tissue, or from other sites of healthy tissue in the mammal, as well as from bone marrow, embryos, placentas, umbilical cords and even adipose tissue.

Using standard cell culture techniques and conditions, the cells are then grown in culture until confluent and used when needed. The cells are preferably cultured only until a sufficient number of cells have been obtained for a particular application.

In addition, these cells can also be frozen and stored in liquid nitrogen until ready to be used.

If cells are used that may elicit an immune reaction, such as human muscle cells from an immunologically distinct donor, then the recipient can be immunosuppressed as needed, for example, using a schedule of steroids and other immunosuppressant drugs such as cyclosporine. However, the use of autologous cells can avoid such an immunologic reaction.

Cells can be obtained directly from a donor, washed and suspended in a selected coating solution before being incorporated into the cell delivery system. To enhance cell viability, the cells are generally added or mixed with the coating solution just prior to incorporation into the delivery system.

Cells obtained by biopsy are harvested, cultured, and then passaged as necessary to remove contaminating, unwanted cells. The isolation of chondrocytes and osteoblasts is described in the examples below. The isolation, culturing, and passaging of central nervous system stem cells, e.g., brain, spinal cord, autonomic nervous system cells, and neuroendocrine cells (that are maintained in an undifferentiated state) is also described below.

Cell viability can be assessed using standard techniques including visual observation with a light or scanning electron microscope, histology, or quantitative assessment with radioisotopes. The biological function of the cells incorporated into the delivery system can be determined using a combination of the above techniques and standard functional assays.

Examples of cells that can be stored and delivered with the delivery system and subsequently grow new tissue include epidermal cells; chondrocytes and other cells that form cartilage ("cartilage-forming cells"); macrophages; dermal cells; muscle cells; hair follicles; fibroblasts; organ cells; macrophages; osteoblasts, periosteal cells, and other cells that form bone ("bone forming cells"); endothelial cells; mucosal cells, e.g., nasal, gastric, bladder and oral mucosal cells; pleural cells; ear canal cells; tympanic membrane cells; peritoneal cells; Schwann cells; corneal epithelial cells; gingiva cells; tracheal epithelial cells; and neural cells, including neural stem cells and neurons, e.g., from the brain, spinal cord, and autonomic nervous system.

Neural stem cells for use in the delivery system and in methods for storage and delivery of cells can be isolated from a variety of nervous system tissues. For example cells can be isolated from spinal cord tissue, brain tissue, and other central nervous system tissues, as well as from peripheral nervous tissues, autonomic nervous system tissues. The peripheral nervous tissue stem cells arise from the CNS in the spinal cord gray matter, and can be isolated as described herein for the isolation of neural stem cells from the spinal cord. Postganglionic autonomic nervous system stem cells (outside the spinal cord) can be isolated as described herein from various tissues, for example, from any innervated organs, such as heart, kidney, small intestine, liver, lung, and bladder tissues. Pre-ganglionic autonomic nervous system stem cells are located in the gray matter of the spinal cord and therefore are isolated in the same way as, and in conjunction with, spinal cord stem cells.

Neuroendocrine stem cells are found in areas such as the adrenal medulla and differentiate into cells that make catecholamines such as epinephrine and norepinephrine, and also from the pancreas, in which case they develop into cells that secrete insulin (beta cells) or glucagon (alpha cells). Other sources of neuroendocrine cells are the parathyroid, pituitary, and the hypothalamus glands. These cells can be isolated from adult mammals, e.g., humans, in the same manner as post-ganglionic autonomic nervous system stem cells, and can be used to prepare tissue constructs used to treat endocrine diseases such as diabetes.

The isolated cells must be undifferentiated, in that when exposed to various growth factors the cells can be differentiated into neurons, oligodendrites, astrocytes, and other nerve tissues. The cells can be isolated from adult nervous tissue, although fetal nervous tissue can also be used.

If the nervous tissue to be repaired or augmented is spinal cord tissue, the nerve cells used in the delivery system can be isolated from spinal cord tissue. Likewise, cell delivery systems containing neural stem cells used to repair brain tissue defects can include neural cells isolated from brain tissue. However, if stem cells obtained from neural tissues are sufficiently undifferentiated, these cells can be used to treat any nervous system defect, because they can be induced to differentiate into the particular kinds nervous tissue required. Stem cells from bone marrow, placentas, umbilical cords and adipose tissue are a possible source of such undifferentiated cells.

The isolated stem cells are maintained in culture, including cytokines such as epidermal growth factor and basic fibroblastic growth factor, in an undifferentiated state by repeated trituration at each passage (e.g., weekly). Once the isolated neural stem cells begin to multiply in culture, they also begin to coalesce to form neurospheres that contain numerous undifferentiated cells. The key to maintaining these cells in an undifferentiated state is to triturate the cells before they begin sending out axons and dendrites. The trituration process should be carried out every 5 to 10 days; weekly intervals appear to be satisfactory. This repeated trituration and passaging enables the isolated, undifferentiated neural stem cells to be cultured indefinitely.

Optionally, the cell delivery system itself can contain at least one cell culture additive. In such a case, one or more additives may be incorporated into the fibers of the article. Preferably, the additives to be incorporated into the fibers will be mixed with the bioabsorable material, e.g., polymer, prior to formation of the fibers.

In loading the additives, the additive may need to be dissolved in a solvent that may not be compatible with the solvent used in the electrospinning process. A block copolymer, acting as a surfactant, can then be used to circumvent this difficulty. One block that forms the micellar shell is a polymer that is compatible with the fibrous material that will be used to form the nano-fibers and the other block that has a different chemical composition is more compatible with the additive. For example, a block copolymer of PLA-co-PEG (polyethylene glycol) could form a micelle that is compatible with the PLA solution while the inner PEG core that is more hydrophilic can be used to load more hydrophilic additives. The micellar property and uptake capacity can be determined by the chemical composition of the blocks, the molecular architecture, the block length, and the chain length ratio of the blocks. The micelles, being compatible with the fibrous material can be incorporated into the nano-fibers during processing. Furthermore, the release rate can also be controlled by the micellar property. For example, a glassy core can reduce the release rate.

By the terminology "cell culture additive" is intended any substance or mixture of substances which may have an affect on cellular growth and nourishment, promotion or inhibition of cellular attachment to other tissue or to the fibrous matrix, or protection of the cells from attack by the host immune system or foreign influences e.g., bacteria, viruses or other pathogens. Thus cell culture additives can include, for example, drugs, enzymes, proteins, peptides, glycoproteins, hormones, sugars, vitamins and growth factors.

Examples of classes of such additives that can be used in accordance with the present invention include antimicrobials, analgesics, antipyretics, anesthetics, antiepileptics, antihistamines, anti-inflammatories, cardiovascular drugs, diagnostic agents, sympathomimetic, cholinomimetic, antimuscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of additives can be used in accordance with the present invention.

Although the discussion that follows is directed to layered structures or membranes in accordance with the invention, it should be understood that the discussion is applicable to other three dimensional articles, including, but not limited to tubes, rods, plugs, blocks, etc.

In one aspect the invention is directed to cell delivery systems which include a fibrous matrix containing multiple, i.e., 2 or more, layers of biodegradable and/or bioabsorbable membranes having a controlled biodegradation rate. The alternative of an extra porous diffusable layer for exchange of nutrients/oxygen and carbon dioxide is also included. The chemical composition, i.e., specific polymers or blends of polymers (including monomers), the fiber diameter, the membrane morphology, the molecular weight distribution and the porosity of the membrane can be used to control the degradation, the hydrophobicity and/or the absorption time of the cells for the membrane. As such, the membranes containing cell culture additives within the fibers themselves are well suited for controlled release of the additives, since the above-mentioned factors can also be used to control the rate of release of the additives.

The membranes can also contain a plurality of fibers which have different additives or different concentrations of additives. Such membranes offer unique cell culture environments with combinations of additives and release profiles.

In one embodiment, the membranes can contain a plurality of biodegradable and/or bioabsorbable non-woven layers. The layers can have the same or different chemical composition, fiber diameters, membrane morphology and porosity as discussed more fully above. Multiple layered membranes, include layered monomers or hydrogels, can offer yet another way to precisely control degradation and release rates.

In such an embodiment, it is also contemplated that additives can be incorporated between the layers of the multi-layered membrane, instead of or in addition to, incorporating the agents into the fiber structure itself.

In one embodiment, the membrane can be attached to a non-absorbable reinforcement layer, such as a Marlox mesh.

In another aspect, the invention relates to a cell delivery system formed by electrospinning different fibers of different materials, in which the system contains a composite of different fibers containing fibers of at least one biodegradable material and fibers of at least one non-biodegradable material.

The cell delivery system containing membranes in accordance with the present invention may be used for guided tissue regeneration. For example, the system may be used to cover internal perforations, such as, for example, perforations in blood vessels, internal organs, the nasal septum, and the eardrum membrane, and may be used to reconstruct the abdominal wall, or to reinforce areas prone to or showing scar formation, such as, for example, inguinal hernias. The system therefore acts as a patch for covering the perforation while delivering cells to the damaged area until healing is complete. Thereafter, the membranes are absorbed by the host biosystem.

Since the cell delivery system can support many different kinds of precursor cells and the support structures, i.e., the fibrous matrix, can guide the development and shape of the new tissue, the delivery system can be used in any instance in which it is desirable to generate new tissue. Particular applications that are described below relate to the generation of cartilage, bone, and neural tissues.

Treatment of Cartilage Defects

Cartilage is a specialized type of dense connective tissue consisting of cells embedded in a matrix. There are several kinds of cartilage. Hyaline cartilage is a bluish-white, glassy translucent cartilage having a homogeneous matrix containing collagenous fibers which is found in articular cartilage, in costal cartilages, in the septum of the nose, and in the larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is found primarily in the epiglottis, the external ear, and the auditory tube. By harvesting the appropriate chondrocyte precursor cells, any of these types of cartilage tissue can be grown using the methods of the invention.

For example, new tissue can be grown for a cartilage meniscus replacement in the knee. The cell delivery system can be formed or cut into the shape of the meniscus to be replaced. The system is then delivered via an arthroscope into the knee joint and positioned in the proper orientation. The cell delivery system containing the chondrocyte precursor cells permits diffusion of nutrients and waste products to and from the entrapped chondrocytes. Over time, e.g., over a period of approximately six weeks, the chondrocytes will become vascularized and the chondrocytes will grow new cartilaginous tissue that takes the shape of the meniscus and engrafts to existing tissue. Eventually, the fibrous matrix of the system will be absorbed by the body.

Treatment of Bone Defects

In another example, periosteal cells (i.e., bone-forming cells) can be used in the invention to fill bone defects or to prepare entire new bones. The cell delivery system can be formed from polymer fibers, cut into the desired size and shape, and positioned within the bone defect. If necessary, adhesives can be used to adhere the delivery system to the bone within the bone defect. The fibrous matrix suspends and maintains the cells, which subsequently grow bone tissue and fill in the bone defect. The fibrous matrix can be used to guide the growth and development of the new bone tissue.

A two dimensional polymer/cell/biological gel (e.g., HA) sandwiched structure can offer an added advantage for construction of more complex three dimensional scaffolds. For example, a plug shaped scaffold can be provided to fill a hole in an animal bone. A sandwiched PLA/cell/HA membrane can be formed into various three dimensional shapes, such as a block, a plug or a tube as shown in FIG. 1. The HA phase will be dissolved rapidly in the body, leaving behind an open channel for transportation of nutrients, oxygen and proteins that are critical for cells to grow. Other shapes of scaffolds such as blocks, tubes, discs and more complex structures can also be produced using a similar stacking technique. The HA layer also acts as a biocompatible adhesive. The major advantage of the scaffold created by this technology is that the hierarchical structures (fiber—nanoscale; pore size—mesoscale; HA layer—microscale) can be precisely controlled.

It is also possible to incorporate arginine-glycine-aspartic (RGD) tripeptides in the scaffolds to improve the adhesion between bone cells and scaffolds. The RGD peptides are known to mediate adhesion of cells in a rather universal way. The benefits of using RGD peptides in bone regeneration are several: these peptides can bind osteoblasts, stimulate their adhesion and proliferation, and trigger biological tissue regeneration.

To facilitate the biomineralization process during bone healing, it should be beneficial to add a small amount of hydroxyapatite (HAP) nanocrystals in the fibrous matrix of the delivery system. It is believed that the presence of HAP can improve the structural stability of the scaffolds and mediate the degradation behavior of the matrix. Electrospinning can be used to incorporate HAP nanocrystals into the scaffolds structure.

It is well known that bone regeneration involves a multitude of cells (e.g. cartilage, fibroblasts, endothelial, etc.) besides osteoblasts. The present invention can be used to deliver stem cells which offer the potential to give rise to all these different types of cells in the bone repair process.

Treatment of Nervous Tissue Defects

In other examples, the cell delivery system can include cells that generate central nervous tissue, including brain tissue, spinal cord tissue, peripheral nerves, autonomic nerves, and neuroendocrine cells. The system can be implanted into a patient having a spinal cord or brain defect following a stroke or other injury. The fibrous matrix then guides the growth and development of the newly-generated neural tissue. The defect in the nervous tissue may result, for example, from a disease, physical trauma, reperfusion injury, ischemia, or infection. However, any defect in nervous tissue can be treated using the cell delivery system.

The cell-delivery system containing neural stem cells can be used to treat defects in nervous tissue throughout the body. For example, infracted brain tissue, damaged or severed nerve tissues in the spinal cord, or autonomic nerves, can all be treated by replacing the damaged tissue by delivering the neural stem cells to a desired area.

Initially, the area and boundaries of the defective nervous tissue is defined, for example, using MRI, CAT scan, PET scan, evoked electrical potentials, or blood flow analysis. Once the outer boundaries of the defective, i.e., damaged or injured nervous tissue are defined, the damaged or injured tissue is surgically removed with a clean cut to create a cavity, leaving normal healthy nervous tissue at the boundaries of the cut (the edges or surfaces of the cavity). Grey matter cells are removed from the healthy tissue surrounding the damaged tissue and cultured to produce isolated neural stem cells that are cultured, expanded, and passaged to provide a sufficient number of cells for treatment.

While the isolated neural stem cells are being cultured and expanded, e.g., for a 7 to 14 day period, an inert, biocompatible spacer (e.g., of calcium alginate) that is designed to induce no or minimal inflammatory responses, is preferably inserted into the space created by removal of the damaged nervous tissue. This biocompatible spacer can be permeated with drugs such as growth factors, anti-inflammatory compounds such as steroids, and/or other pharmaceutical agents designed to prevent fibrous tissue from growing into the space created by the removal of the damaged tissue.

Once the autologous cells have been expanded to a sufficient number of cells, the cell delivery system is prepared as described herein and is formed into the shape of the removed damaged tissue. The system is then implanted into the space remaining after the spacer is removed. Of course, if cultured neural stem cells are available for immediate implantation, no spacer is required.

Although it is preferred that surgery occur as soon after the injury to the nervous system tissue as possible, the new methods can be used to treat injuries that occur several weeks to months prior to surgery, as long as the surgery leaves a clean cut exposing healthy nervous tissue on either side of the implanted support structure. Autologous cells can also be removed from sites other than the surgery site where the damaged nervous tissue is removed.

Any localized damage or trauma to nervous system tissue can be repaired, including infracts, tissue damage caused by cancer, stroke, or wounds such as gunshot wounds or other crushing or slicing injuries. Furthermore, various nervous system diseases such as Parkinson's disease can be treated by implanting the cell delivery system including neural stem cells engineered to include a gene that expresses a protein that is missing in the diseased patient.

Additional Uses of Neural Stem Cells

Neural stem cells isolated from the CNS, e.g., the cortex, striatum, and spinal cord, as well as the automatic nervous system (ANS), can also be used as "smart cells" that assist in orchestrating the organization and development of other engineered tissues, for example, in artificial organs such as the kidneys, liver, bowel, and bladder, by including these neural stem cells in a mix of precursor cells used to prepare tissue engineered organs.

Neurodegenerative processes such as Parkinson's disease can be treated with autologous neural stem cells that are genetically engineered using standard techniques to produce dopamine (or with naturally occurring stem cells that make dopamine), and incorporated into the delivery system. Such hydrogel-neural stem cell compositions will function longer after implantation than an injected suspension of cells.

Similarly, genetic neurodegenerative processes, such as the leukodystrophies, can be treated with neural stem cells that have been genetically repaired.

In addition, neuroendocrine stem cells can be isolated from the adrenal medulla or the pancreas and used to prepare endocrine tissue constructs to treat endocrine disorders such as diabetes.

It is also contemplated that the delivery system containing skin cells may be employed as a cover for burns, whereby the device acts as a patch until the burn is healed.

The delivery system of the present invention may be employed as a scaffolding to treat ulcers. A porous membrane can be designed to stimulate the proliferation of fibrous tissue, as a consequence of which, for example, in the case of ulcers, the wound bed becomes more optimal for the regeneration of skin.

The delivery system of the present invention may also be employed in redirect healing, whereby one side contains a membrane which is rapidly absorbed allowing the cells being delivered to participate in the healing process, and the other side contains a membrane designed to protect nerves and organ coverings, and mucosa during the healing process, whereby the formation of fibrous tissue over such nerves, organs, and mucosa is prevented.

The delivery system may similarly be employed in covering denuded epithelial surfaces or weakened areas such as damaged middle ear mucosa or other mucosal surfaces, thinned vascular walls, or surgically denuded areas, such as, for example, surgically denuded areas of the pelvis.

The delivery system may also function as an anti-fibroblastic growth barrier, or as nerve coaptation wraps for connecting or repairing severed nerve ends or for repairing inflamed nerves, while supplying new cells to contribute to the healing process.

The fibrous matrix of the present invention may first be formed or constructed into various shapes including, but not limited to, flat sheets, tubes, rods or other three dimensional articles, as necessary to facilitate use in a particular application. A dispersion of viable cells can be added to the matrix, e.g. coated on the surface, and a thin membrane layer can be added to contain the cells.

A cell delivery system of the present invention is generally used in the form of a sheet of a desired size and shape. A surgeon may cut a custom shape from preformed sheets to suit particular applications. After the sheet is shaped for a suitable fit, the flexible nature of the sheet enables the surgeon to conform the sheet to fit around the desired area for implantation. The system can be formed into a strip which wraps around an organ, e.g., an intestine. The cell delivery system according to the present invention can incorporate ties or straps which connect to the system and which are used to tie or otherwise secure the system to a desired area. It is further contemplated that the system of the present invention may be affixed to the implantation site by surgical fasteners or sutures. The flexible nature of the present system allows the system to flex and bend along with normal movements of the body without being overly restrictive.

In another aspect, the invention is directed to a method for storage of living cells for delivery to a mammal. The method includes:
(a) providing a cell delivery system which contains:
   (i) viable cells; and
   (ii) a biodegradable and/or bioabsorbable fibrous matrix as a carrier physically associated with the cells to contain and release the cells at a controlled rate;
(b) cooling the cell delivery system down to a preservation temperature under conditions which maintain the integrity of the system; and
(c) maintaining the cell delivery system at or below the preservation temperature until a time when cell delivery is desired.

The preservation temperature is preferably below at least about −50° C., more preferably at least about −70° C., and most preferably at least about −180° C. The cooling step can be carried out by first placing the cells in a styrofoam container at −70° C. overnight (at a cooling rate of −1° C./min from room temperature to −70° C.), then transferring the cells into liquid nitrogen for long term storage. The cooling step is preferably carried out by submerging the cell delivery system in liquid nitrogen.

One advantage of the cell/delivery system according to the invention is that the electrospun membrane exhibits excellent flexibility and handling ability in liquid nitrogen. Unlike typical cell storage scaffolds such as polymer films, foams and gels, when inserted in a liquid nitrogen environment, they often become brittle and cannot be handled easily. Electrospun membranes exhibit excellent mechanical handling ability even when frozen. In liquid nitrogen, the membranes retain some degree of flexibility and never become brittle. Full flexibility is recovered immediately at room temperature. It is believed that electrospun scaffolds according to the invention offer superior storage capability in liquid nitrogen than other scaffolding forms or materials.

In yet another aspect, the invention is directed to a method for delivery of viable cells to a mammal. The method includes:
(a) providing a cell delivery system containing:
   (i) viable cells; and
   (ii) a biodegradable and/or bioabsorbable fibrous matrix as a carrier physically associated with the cells to contain and release the cells at a controlled rate; and
(b) positioning the cell delivery system at a desired location for cell delivery to the mammal.

Specific examples of cells that can be delivered and specific applications are discussed above.

The embodiments of the cell delivery system having a thin layered structure as described herein are well-suited for application by techniques involving endoscopy. Endoscopic surgical procedures involve the use of cannulas or tubes which provide narrow openings into a body and allow minimally invasive access to surgical targets. In laparoscopic procedures, surgery is performed in the interior of the abdomen through small tubes inserted therein. Endoscopes are frequently used as viewing devices inserted through the cannulas which allow surgeons to see the interior of the body.

Certain endoscopic and laparoscopic procedures may require that the surgical region be insufflated. Accordingly, any instrumentation inserted into the body should be substantially sealed to ensure that gases do not enter or exit the body through the incision. Moreover, endoscopic and laparoscopic procedures often require the surgeon to operate on organs, tissues and/or vessels far removed from the incisions. Thus, instruments used in such procedures are typically long and narrow while being functionally controllable from a proximal end of the instrument.

In accordance with the present invention any apparatus for deploying and positioning the cell delivery system disclosed herein may be inserted through a cannula and deposited at a target site. Once the system is positioned as desired, it may optionally be sutured, stapled or otherwise fastened to the target site with instruments designed to be inserted through a cannula.

Nanofiber Fabrication Technique for Biodegradable and/or Bioabsorbable Polymers: Electrospinning Membranes with Different Biodegradable and/or Bioabsorbable Fibers The membranes useful as the fibrous matrix according to the present invention are preferably produced by electrospinning using a multiple jet system. Preferably, the multiple jet system includes a matrix of spinnerets for introducing conducting fluid containing the biodegradable and/or bioabsrobable fiberizable material. The use of a multiple jet system to produce membranes in accordance with the invention is possible by having independent control over different jets. Thus, different jets can produce different fibers as discussed more fully above.

Moreover, sub-micron diameter fibers can be produced in accordance with the invention at a relatively high yield. For example, a 40% polymer solution being spun from a single spinneret with a diameter of 700 microns, which results in a final filament having a diameter of 250 nm, will have an effective draw ratio of $7.84 \times 10^6$. If the extrudate (conducting fluid) from each spinneret has a rate of about 10 μl/min, the final filament speed will be about 136 m/s for each spinneret, which is a relatively high spinning rate. Thus, a commercially viable process for making membranes according to the invention is achievable with a sufficient number of spinnerets operating at such speeds.

The conducting fluid will preferably include a solution of the polymer materials described more fully above. The polymer material used to form the membrane is first dissolved in a solvent. The solvent can be any solvent which is capable of dissolving the polymer and providing a conducting fluid capable of being electrospun. The solvent is preferably selected from N,N-Dimethyl formamide (DMF), tetrahydrofuran (THF), N-N-dimethyl acetamide (DMAc), methylene chloride, dioxane, ethanol, chloroform, water or mixtures of these solvents.

The conducting fluid can optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$, or mixtures of these salts. Calcium phosphate and calcium hydroxyapetite can also be incorporated.

The polymer solution forming the conducting fluid will preferably have a polymer concentration in the range of about 1 to about 80 wt %, more preferably about 10 to about 60 wt %. The conducting fluid will preferably have a viscosity in the range of about 50 to about 2000 mPa·s, more preferably about 200 to about 700 mPa·s.

The electric field created in the electrospinning process will preferably be in the range of about 5 to about 100 kilovolts (kV), more preferably about 10 to about 50 kV. The feed rate of the conducting fluid to each spinneret (or electrode) will preferably be in the range of about 0.1 to about 1000 microliters/min, more preferably about 1 to about 250 microliters/min.

Figure 2:
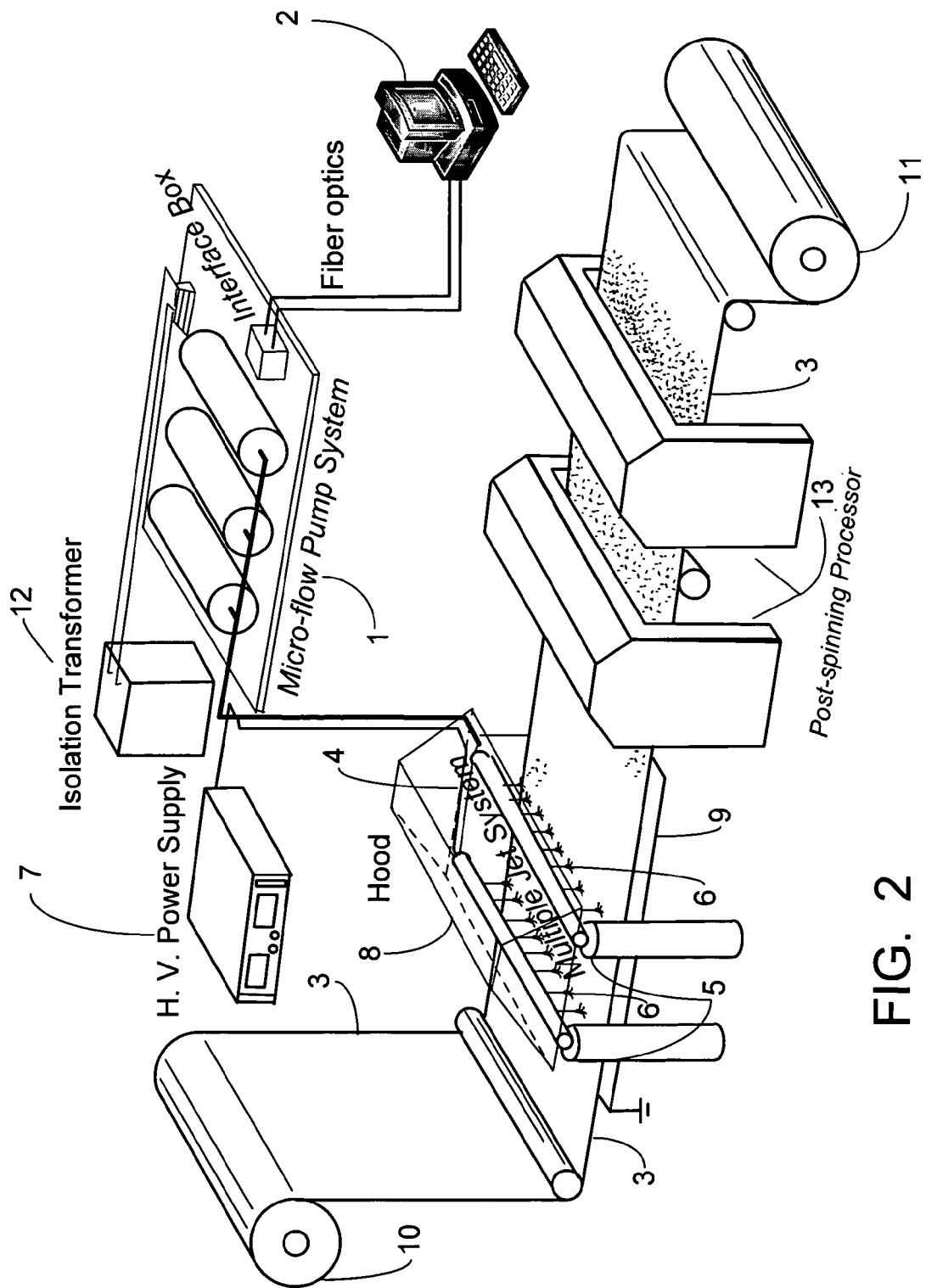
FIG. 2 is a schematic of an electrospinning system.
Figure 3:
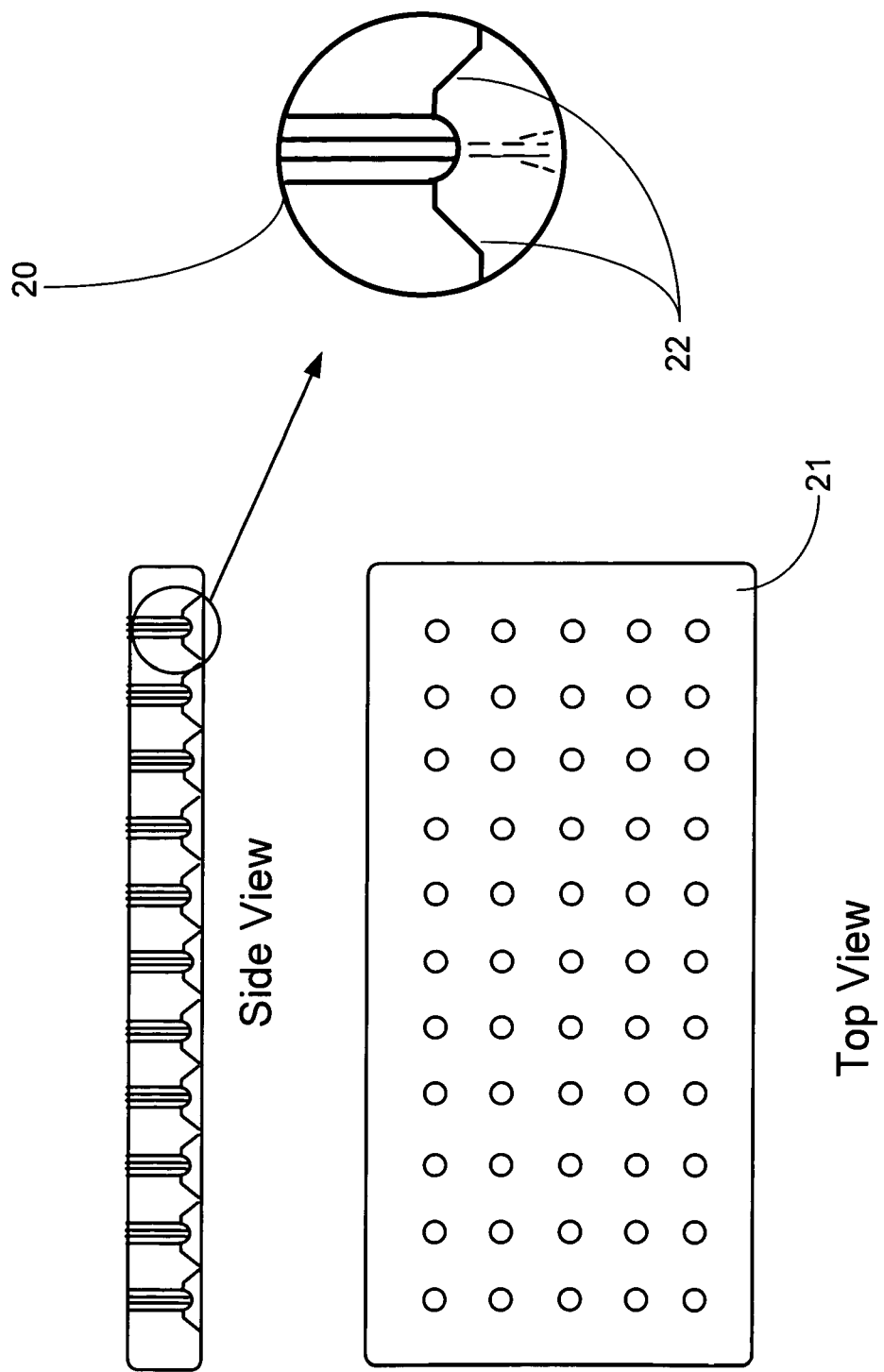
FIG. 3 is a schematic of an array of spinnerets for an electrospinning process.

A particular apparatus for producing membranes for the cell delivery system according to the present invention, which uses a multiple jet electrospinning system, is shown schematically in FIG. 2. Equipment not essential to the understanding of the invention such as blowers, heat exchangers, pumps and compressors and the like are not shown.

Referring now to FIG. 2, the conducting fluid, which contains the biodegradable polymer, is supplied by a micro-flow pump system 1. The conducting fluid preferably contains a biodegradable polymer, a solvent and a salt, e.g., 25 wt % PLA-DMF solution with 1 wt % $KH_2PO_4$. Optionally, one or more cell culture additives can be incorporated into the conducting fluid. The pump system 1 is linked to a computer 2 which controls the flow rate of the conducting fluid to selected spinnerets by controlling pressure or flow rate. The flow rate can be changed depending upon the speed of the support membrane 3 and the desired physical characteristics of the membrane, i.e., membrane thickness, fiber diameter, pore size, membrane density, etc.

The pump system 1 feeds the conducting fluid to a multiple jet system 4 that contains manifolds 5 having a bank of spinnerets 6. A charge in the range of about 20 to about 50 kV is typically applied to the spinnerets by a high voltage power supply 7. A hood 8 is positioned over the multiple jet system 4 to remove the solvent at a controlled evaporation rate.

A ground plate 9 is positioned below the multiple jet system 4 such that an electric field is created between the charged spinnerets 6 and the ground plate 9. The electric field causes tiny jets of the conducting fluid to be ejected from the spinnerets and spray towards the ground plate 9, forming small, e.g., sub-micron, diameter filaments or fibers.

A moving support 3 is positioned between the charged spinnerets 6 and the ground plate 9 to collect the fibers which are formed from the spinnerets and to form an interconnected web of the fibers. The support 3 moves in the direction from the unwind roll 10 to the rewind roll 11.

The micro-flow control/pumping system is electrically isolated from the ground and is powered by an isolation transformer 12.

The post-spinning processors 13 have the functions of drying, annealing, membrane transfer (for example, from a stainless steel mesh substrate to another substrate, e.g., a Malox mesh) and post conditioning.

Multiple jets with designed array patterns can be used to ensure the fabrication of uniform thickness of the membrane. Hood, heating and sample treatment chambers can also be included to control the solvent evaporation rate and to enhance the mechanical properties. The recovered thickness can be precisely controlled from tens of microns to hundreds of microns. While additional embodiments or modifications to the electrospinning process and apparatus are described below, a more detailed description of an apparatus and method for electrospinning polymeric fibers is set forth in co-pending, commonly owned patent application Ser. No. 09/859,004, entitled "Apparatus and Methods for Electrospinning Polymeric Fibers and Membranes," filed on May 16, 2001 and incorporated herein for all purposes by reference.

Variation of Electric/Mechanical Properties of Conducting Fluid

The properties of the resulting membrane produced by electrospinning will be affected by the electric and mechanical properties of the conducting fluid. The conductivity of the macromolecular solution can be drastically changed by adding ionic inorganic/organic compounds. The magneto-hydrodynamic properties of the fluid depend on a combination of physical and mechanical properties, (e.g., surface tension, viscosity and viscoelastic behavior of the fluid) and electrical properties (e.g., charge density and polarizability of the fluid). For example, by adding a surfactant to the polymer solution, the fluid surface tension can be reduced, so that the electrostatic fields can influence the jet shape and the jet flow over a wider range of conditions. By coupling a pump system that can control the flow rate either at constant pressure or at constant flow rate, the effect of viscosity of the conducting fluid can be controlled.

Electrode Design

In another method for producing membranes for use in the cell delivery system, the jet formation process during electrospinning is further refined to provide better control over fiber size. Instead of merely providing a charged spinneret and a ground plate, a positively charged spinneret is still responsible for the formation of the polymer solution droplet and a plate electrode with a small exit hole in the center is responsible for the formation of the jet stream. This exit hole will provide the means to let the jet stream pass through the plate electrode. Thus, if the polymer droplet on the positively charged spinneret has a typical dimension of 2-3 mm and the plate electrode is placed at a distance of about 10 mm from the spinneret, a reasonable electrostatic potential can be developed. The short distance between the two electrodes implies that the electrostatic potential could be fairly low. However, the resultant electric field strength could be sufficiently strong for the electrospinning process. By varying the electric potential of individual spinnerets, the jet formation can be controlled and adjusted for individual spinnerets. Such an electrode configuration should greatly reduce the required applied potential on the spinnerets from typically about 15 kilovolts (kV) down to typically about 1.5 to 2 kV (relative to the ground plate potential). The exact spinneret potential required for stable jet formation will depend on the electric/mechanical properties of the specific conducting fluid.

Control of Jet Acceleration and Transportation

In another method for producing membranes for use in the cell delivery system, the jet stream flight of individual spinnerets is also precisely controlled. The jet stream passing through the plate electrode exit hole is positively charged. Although this stream has a tendency to straightening itself during flight, without external electric field confinement the jet will soon become unstable in its trajectory. In other words, the charged stream becomes defocused, resulting in loss of control over the microscopic and macroscopic properties of the fluid. This instability can be removed by using a carefully designed probe electrode immediately after the plate electrode and a series of (equally) spaced plate electrodes. The electrode assembly (i.e., the probe electrode and the plate electrodes) can create a uniform distribution of electrostatic potential along the (straight) flight path. The acceleration potential is formed by placing the base potential of the spinneret at about +20 to +30 kV above the target (at ground potential) while the electrostatic potential of the probe electrode can be adjusted to slightly below the plate electrode base potential. The composite electrodes are capable of delivering the jet stream to a desired target area.

Jet Manipulation

In yet another method for producing membranes for use in the cell delivery system, individual jet streams can be focused by using an "Alternating Gradient" (AG) technique. The basic idea is to use two pairs of electrostatic quadrupole lenses. The second lens has the same geometric arrangement as the first lens with a reversed (alternate) electric gradient. The positively charged jet stream will be focused, for example, in the xz plane after the first lens and then be refocused in the xy plane after the second lens. It is noted that the z-direction represents the direction of the initial flight path. By applying an additional triangle-shaped waveform to the potential on one of the pairs of the quadrupole, the jet can be swept across the target area, allowing the control of the direction of the jet stream. Furthermore, with varying waveform of the 'sweep' potential, a desired pattern on the target can be formed.

Pattern Design by Electrospinning

In yet another method for producing membranes for use in the cell delivery system, reference will be made to FIG. 3. In this method, the conducting fluid is introduced into the electrospinning process through an array of electrospinning spinnerets 20. The array of electrospinning spinnerets are assembled in a matrix 21 that provides electrical isolation for the spinnerets, with each spinneret having two pairs (x and y direction) of miniature scanning electrodes 22. The spinneret 20 and the scanning electrodes 22 are electrically wired such that each individual polymer solution jet can be turned on and off and be steered to a finite size target area. As each spinneret 20 can be turned on/off independently by electricity, the response time will be relatively fast. Also, each spinneret 20 can deliver a different solution, e.g., each containing a different polymer or different additive or concentration of additive. A designed pattern can be obtained in the resultant membrane. This pattern can be precisely controlled by a computer and can be tailored for specific applications.

Multiple Jet Slit-Die Geometry

In another apparatus for producing membranes for use in the cell delivery system, reference is made to FIGS. 4(*a*)-4(*c*). In this apparatus, a multiple jet system 30 comprises an array of electrospinning spinnerets 31, each spinneret 31 being defined by a slit 32 formed in a slit-die 33 that is coupled to high voltage to serve as an electrode disposed above the ground plate 34. As shown in detail in FIG. 4(*c*), the spinnerets 31 are each interconnected by selectively narrow slits 35, such that each spinneret 31 is interconnected to a neighboring spinneret 31 by a slit 35. The conducting fluid will not flow through the slits 35, but will flow through each of the spinnerets 31 in a more robust manner.

The slit-die approach permits three distinct advantages that are not available by using individual spinnerets. (1) The slit-die is made up of two separate components with controlled dimensions of the effective openings for the spinnerets. In other words, by changing the distance between the two components, the effective openings of the spinnerets become available. (2) The presence of slits between the larger openings permits fluid flow and thereby equalizes the pressure difference between the spinnerets. (3) The presence of slits can also reduce potential blockage of the fluid.

The membranes produced by the slit-die approach can achieve a larger degree of flexibility in the structures. For example, different size nanofibers can be produced from the same slit-die setup.

Control of Degradation Rate Through Processing Parameters

As discussed above, very different fiber diameter and morphology in the membrane can be obtained by changing the parameters in the electrospinning process. As the degradation rate is inversely proportional to the fiber diameter, the manipulation capability through processing parameters provides not only the means to control the degradation rate of the membrane but also the ways to control loading efficiency for cell culture additives and the release rate for such additives.

For example, it is believed that a change in charge density (through the addition of salts) can significantly affect the fiber diameter. When 1 wt % potassium phosphate ($KH_2PO_4$) was added to a PLA-co-PGA solution, the fiber diameter became much thinner (see SEM picture in FIG. 5) than the one with no salt added (FIG. 6). Thus, it is believed that higher excess charge density generally favors the production of thinner fibers and lower excess charge density favors the production of thicker fibers. Several other kinds of salts (e.g. NaCl, $KH_2PO_4$, KIO and $K_3PO_4$), which are all biologically compatible to the body, are also contemplated.

Cell Delivery System Construction

Once a first membrane is produced as described above, a dispersion of cells can be added to the membrane. Typically, the dispersion of cells is contained in a minimum essential medium solution, which is coated on the surface of the membrane. Any conventional method of coating is acceptable, provided the viability of the cells is not jeopardized. It may be necessary to first dip the membrane into the minimum essential medium solution to improve adhesion of the membrane surface and the cells. This may be required, for example, where the membrane is hydrophobic and the cells are hydrophilic.

After coating the dispersion of cells on the surface of the membrane, a second membrane can be produced to cover and contain the viable cells, which bonds to the surface of the first membrane. The second membrane is typically much thinner than the first membrane and has a porosity which allows transfer to $O_2$ and nutrients into the cells and allows transfer of $CO_2$ away from the cells.

The second membrane can be produced using an apparatus or method described above.

EXAMPLES

The following non-limiting examples have been carried out to illustrate preferred embodiments of the invention. These examples include the preparation of membranes according to the invention, analysis of the membranes and testing of the membranes.

Example 1

A layered cell storage and delivery system containing live bone cells and biodegradable nanofibers was fabricated by using an electrospinning process as follows: First, a 40 wt % poly(D,L-lactide)(PLA) (M.W.=80,000 g/mol)/lactide monomer (144 g/mol) blend solution in N,N-dimethyl formamide (DMF) was prepared by slowly dissolving the polymer/monomer blend into the DMF solvent at room temperature. The solution was then loaded into a 5 ml syringe fitted with a gauge 20 needle, and delivered through a Teflon tube (0.03 inch ID) to the exit hole of an electrode having a diameter of 0.025 inches. The solution was pumped and controlled by a syringe pump (Harvard Apparatus "44" series, MA) at a flow rate of 20 microliters/min. A 20 kV positive high voltage (by Glassman High Voltage, Inc.) was applied on the electrode. The grounded target was a rotating drum having a diameter of about 10 cm and operating at a speed of about 300 rpm. The distance from the tip of the electrode to the outside surface of the drum was about 15 cm. A tiny electrospinning jet was formed and stabilized under these conditions. The electrode was continually moved across the length of the drum and a membrane having an average thickness of about 160 microns was formed as an interconnected web of thin submicron diameter fibers on the surface of the drum. The electrospinning process was operated under a sterilized environment.

After the membrane was formed, it was immediately cut into 1×1 inch squares, and dipped into a minimum essential medium solution (containing 10% Fetal Bovine Serum) to increase the adhesion between membrane surface and the live bone cells. The dipping method was used to facilitate the membrane and cell interactions because the membrane itself was hydrophobic, and the live bone cells were hydrophilic. Without the dipping step, aggregation of the medium solution including live cells would occur in the form of large droplets on the membrane surface. The wet membrane was then placed on the ground collector, and a volume of 30 μl of the bone cells (about 30,000 cells) solution (cell conc.~$10^6$ cells/ml) was deposited onto each 1×1 inch square membrane by a casting method.

The cell containing membrane was then subjected to another electrospinning treatment using the PLA/monomer solution for 10 sec to produce a thin top layer of membrane to encapsulate the bone cells near the surface of membrane. To achieve a fast release of the bone cells, the thickness of the top layer membrane was very thin compared with the thickness of the bottom layer membrane. This process generated a thin top layer/live bone cells/thicker bottom layer "sandwich" structure, which is shown schematically in FIG. 7. Referring to FIG. 7, the final cell/membrane structure consisted of three parts: the bottom layer 40 having the thickness ranging from 120 μm to 200 μm, live cells 41 with dimension from 15~20 μms, and the top layer 42 having a thickness of several microns.

The membranes were placed in individual sterilized petri dishes and slowly cooled down to −100° C. and stored in liquid nitrogen for future use. The membranes stored and preserved in liquid nitrogen did not break or shatter, and their flexibility was recovered upon returning to room temperature.

Example 2

The cell release by the delivery system from Example 1 was tested as follows: the petri dish containing the delivery system was brought to room temperature and 5 ml of the minimum essential medium solution, including Fetal Bovine Serum, was added into the petri dish containing the layered cell/membrane composite. The dish was maintained in an incubator under the following conditions: the temperature was 37° C. in a fully-humidified atmosphere having 5% $CO_2$ in air. Several cell/membrane composites were used for the study. Individual composites were removed from the incubator at different times for cell culture testing using an optical microscopy technique. The number of cells was determined and recorded. The typical cell release and growth mechanism, which was observed visually, is shown schematically in FIG. 8.

Figure 8:
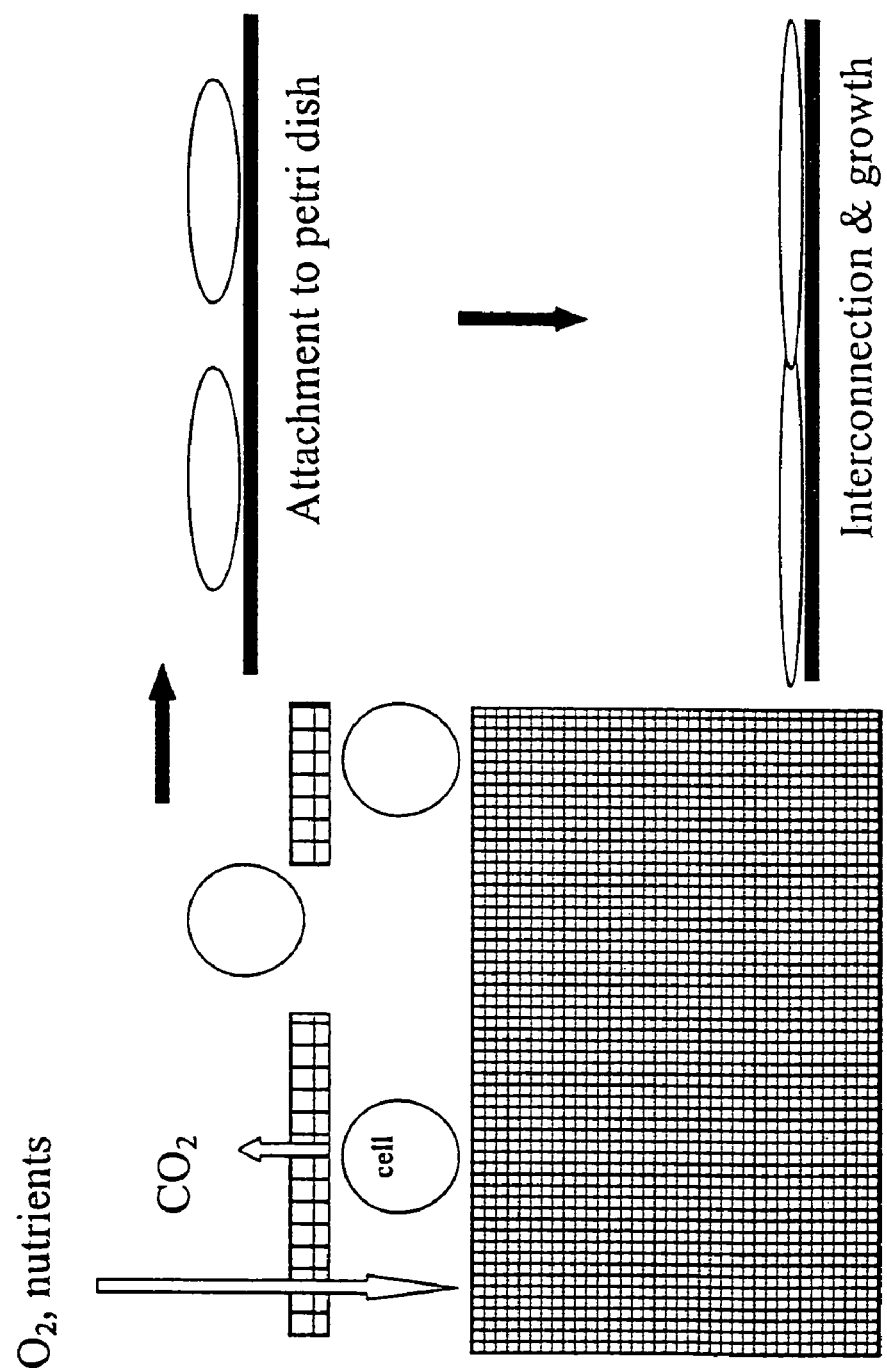
FIG. 8 is a schematic of the cell release and growth mechanism described in Example 2.

Referring to FIG. 8, the embedded cells 50 were found to be able to survive because there were many small pores on the top membrane layer 51 to allow transfer of oxygen and the nutrients to the cells 52. The top membrane 51 was used only as mechanical restraining means without damaging the properties of cells. In the chosen study, the cells started to be released from the membrane 53 in the first day. The released cells 54 would stick to the bottom of the petri dish 55, and the shape of cell was found to change from round to flat 56. After attachment, the cells grew through proliferation.

Figure 9:
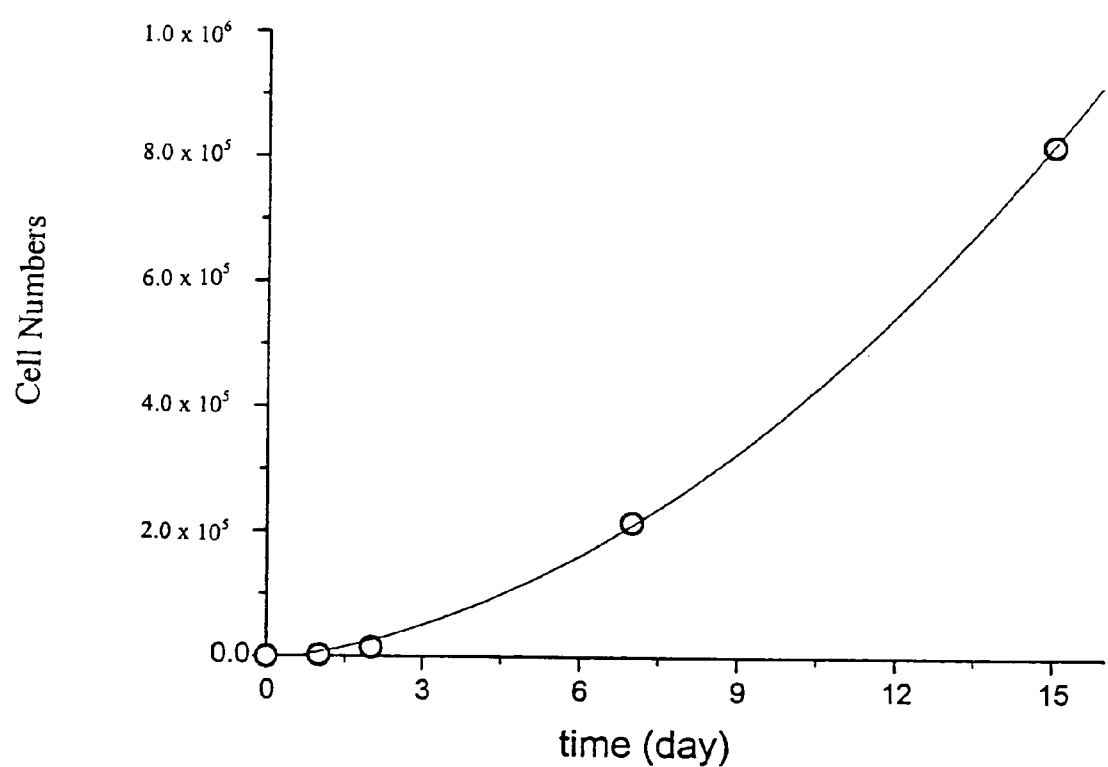
FIG. 9 is a graph showing the growth rate of cells as described in Example 2.

The numbers of cells attached to the petri dish were measured by an optical technique. The results are shown graphically in FIG. 9. A review of FIG. 9 reveals that more than 20% of the cells in the membrane were released in 2 days, and the released cells grew continuously. After 1 week, the cell numbers were found to increase 7 times compared to the number of cells in the initial condition. The optical microscopic photographs of the cells released from the membrane as a function of time also indicate that the PLA membrane has not damaged the cell growth process.

Figure 6:
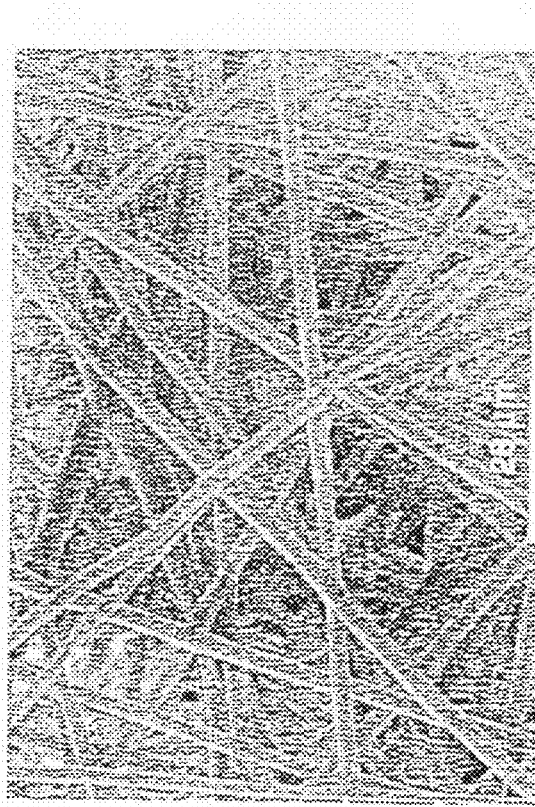
FIG. 6 is an SEM of a PLA-co-PGA membrane spun from a solution without salt added.
Figure 5:
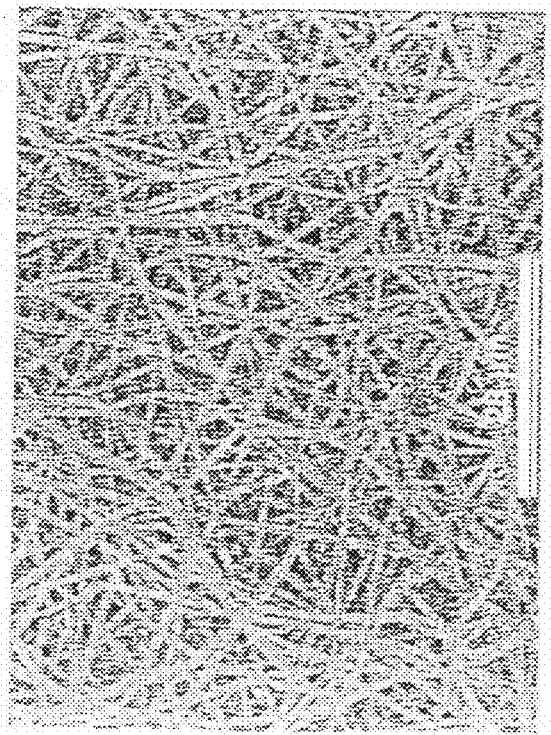
FIG. 5 is an SEM of a PLA-co-PGA membrane spun from a solution containing 1 wt % $KH_2PO_4$.
Figure 10:
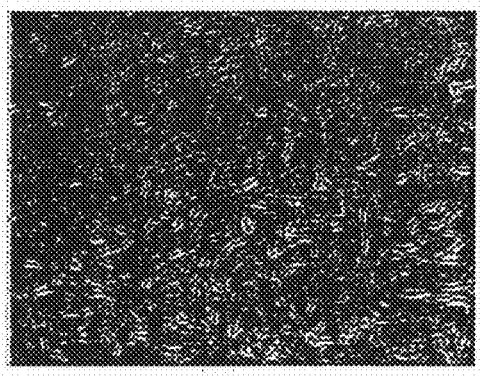
FIG. 10(a) is a microscopic photograph of cells after 2 days of growth as described in Example 2.
FIG. 10(b) is a microscopic photograph of cells after 1 week of growth as described in Example 2.
FIG. 10(c) is a microscopic photograph of cells after 2 weeks of growth as described in Example 2.
FIG. 10(d) is a microscopic photograph of cells after 6 weeks of growth as described in Example 2.
Figure 10:
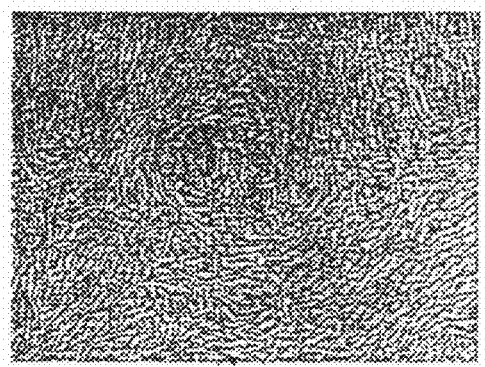
Figure 10:
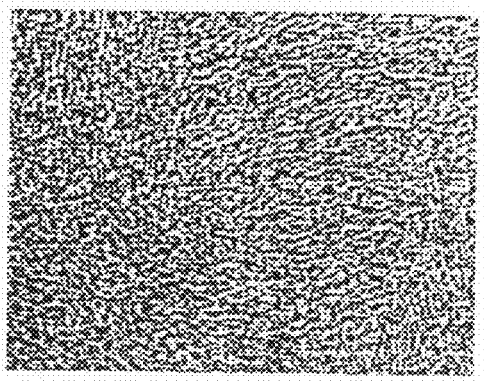
Figure 10:
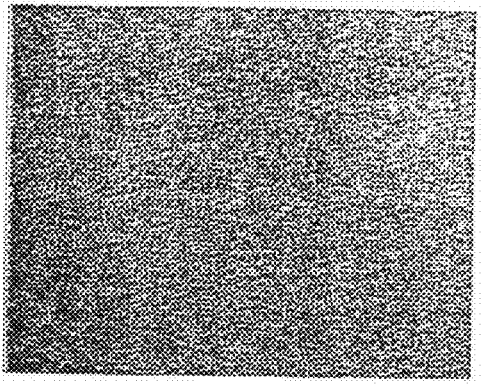

Optical microscopic photographs, taken over time, are shown in FIGS. 10(a)-10(d). The photographs were taken at the following time intervals following the start of incubation: FIG. 10(a)-2 days; FIG. 10(b)-1 week; FIG. 10(c)-2 weeks; and FIG. 10(d)-6 weeks. A review of FIGS. 10(a)-10(d) reveals that the released cells started to form interconnections, which led to more cell growth. The entire petri dish was covered with cells in 1 week. The cells continued to show a more dense population and finally formed a mineralised matrix after 6 weeks.

Example 3

The mechanical properties of an electrospun membrane useful as a carrier in a cell delivery and storage system was evaluated as follows: A PLGA (75/25 PLA:PGA) membrane was produce by a process similar to Example 1. The membrane had a thickness in the range of about 150 microns. The membrane was cut into a 2.5×2.5 cm strip and evaluated for flexibility by holding one end of the strip using forceps and twisting the strip.

Figure 11:
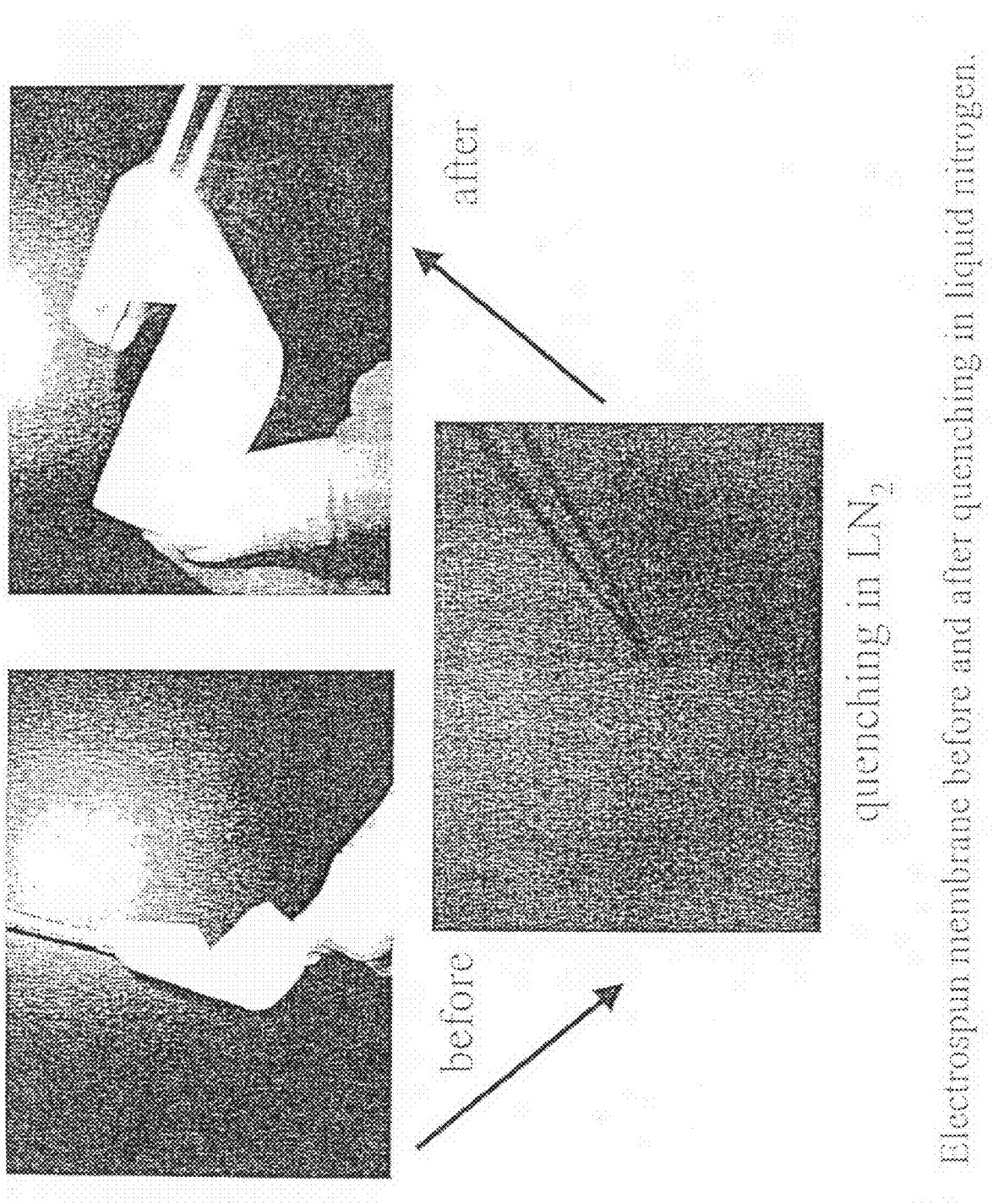
FIG. 11 is an illustration of the flexibility test described in Example 3.

The strip was then quenched in liquid nitrogen for 20 minutes and then removed from the liquid nitrogen. The frozen strip was again evaluated for flexibility. FIG. 11 illustrates the flexibility before and after quenching. The membrane retained significant flexibility and never became brittle or developed cracks when twisted in a frozen state. The full flexibility of the membrane returned upon reaching room temperature.

Example 4

The cell release by a cell delivery system having an electrospun PLGA/lactide matrix carrier after long term storage was tested as follows: A PLGA/lactide (90:10 PLGA:lactide monomer) delivery system containing live bone cells having "sandwich" structure was prepared according to the methods of Example 1. The cell-containing system was placed in a sterile plastic vial and cooled down at rate of 1° C./min to −70° C. using a freezing container (Nalgene Cryo 1° C. freezing container). The plastic vial containing the frozen cell delivery system was maintained at −70° C. for 4 hours. The vial was then removed from the container and inserted into liquid nitrogen for long term preservation. The vial was kept in long term preservation for at least 48 hours.

The vial was then removed from the liquid nitrogen and the cell delivery system was placed in a petri dish containing 5 mls of minimum essential medium at room temperature. The petri dish was then placed in an incubator, which was maintained at 37° C. in a fully-humidified atmosphere having 5% $CO_2$ in air. Optical microscopy was used to monitor the cell release activity. An optical microscopic photograph, taken 3 days after the start of incubation, is shown in FIG. 12.

Figure 12:
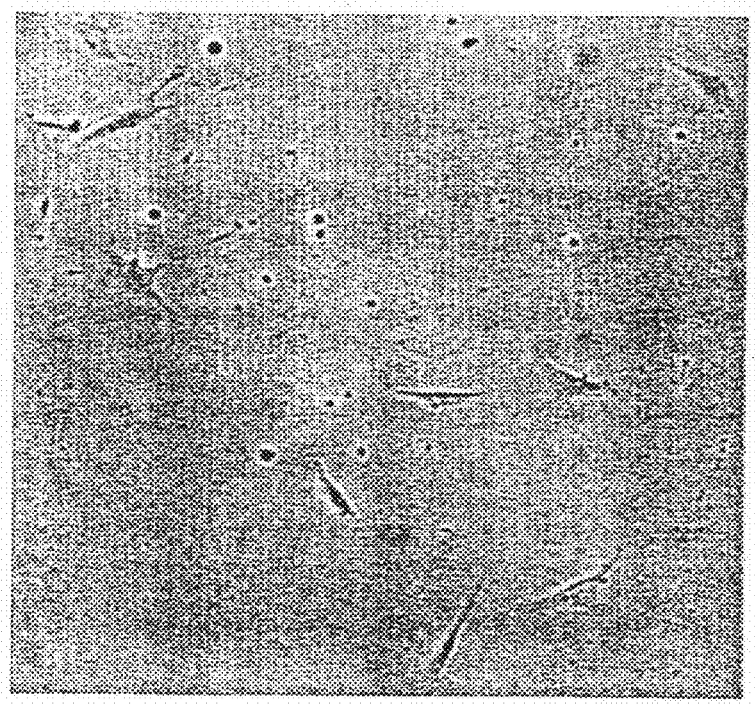
FIG. 12 is a microscopic photograph of live bone cells released from the delivery system after long term storage as described in Example 4.

A review of FIG. 12 shows that a significant portion of living cells was released from the delivery system in 3 days.

Example 5

The wettability of a cell solution on the surface of an electrospun membrane was evaluated as follows: A PLGA/lactide (90:10 PLGA:lactide monomer) membrane was prepare in the manner described in Example 1. Approximately 5 μls of a cell solution containing live bone cells was placed onto the surface of the membrane using an eye dropper and the contact angle of the droplet was measured as a function of time.

The test was repeated using a membrane that had first been dipped into a medium solution. The result of the two tests are shown graphically in FIG. 13.

A review of FIG. 13 reveals that, without pre-wetting the membrane, the contact angle starts out at about 95°. After pre-wetting the membrane, the contact angle decreases to about 60°. Thus, pre-wetting the membrane significantly improves its wettability for the cell solution.

Thus, while there has been disclosed what is presently believed to be preferred embodiments of the invention, those skilled in the art will appreciate that other and further changes and modifications can be made without departing from the scope or spirit of the invention, and it is intended that all such other changes and modifications are included in and are within the scope of the invention as described in the appended claims.

We claim:

1. A method for storage of living cells for delivery into a mammal, said method comprising:
(a) providing a cell delivery system comprising:
(i) viable cells; and
(ii) a biodegradable and/or bioabsorbable fibrous matrix physically associated with said cells to contain and release said cells at a controlled rate, wherein said biodegradable and/or bioabsorbable fibrous matrix contains at least about 20 weight percent of fibers having fiber diameters in the range of about 10 up to about 1000 nanometers of a biodegradable and/or bioabsorbable fiberizable material;
(b) cooling said cell delivery system down to a preservation temperature under conditions which maintain the integrity of said system; and
(c) maintaining said cell delivery system at or below said preservation temperature until a time when delivery is desired.

2. A method according to claim 1, wherein said viable cells are tissue precursor cells selected from the group consisting of differentiated cells obtained from living tissue, cells preselected to differentiate into specific cell types and undifferentiated cells.

3. A method according to claim 1, wherein said biodegradable and/or bioabsorabale fibrous matrix is formed by electrospinning fibers of biodegradable and/or bioabsorbable fiberizable materials.

4. A method according to claim 3, wherein said biodegradable and/or bioabsorbable fiberizable material comprises a biodegradable and/or bioabsorbable polymer.

5. A method according to claim 4, wherein said biodegradable and/or bioabsorbable polymer comprises a monomer selected from the group consisting of a glycolide, lactide, dioxanone, caprolactone, trimethylene carbonate, ethylene glycol and lysine.

6. A method according to claim 4, wherein said biodegradable and/or bioabsorbable polymer comprises a biodegradable and/or bioabsorbable linear aliphatic polyester.

7. A method according to claim 6, wherein said biodegradable and/or bioabsorbable linear aliphatic polyester is a polyglycolide or a copolymer poly(glycolide-co-lactide).

8. A method according to claim 3, wherein said biodegradable and/or bioabsorbable fiberizable material comprises a material derived from biological tissue.

9. A method according to claim 3, wherein said fibers have diameters in the range from about 20 to about 500 nanometers.

10. A method according to claim 1, said cell delivery system further comprising a layered structure which comprises:
a relatively thick base layer of a biodegradable the biodegradable and/or bioabsorbable fibrous matrix,
a dispersion of viable cells dispersed over the surface of said base layer,
a relatively thin top layer of the biodegradable and/or bioabsorbable fibrous matrix covering said dispersion of cells and adhered to the surface of said base layer, said top layer having sufficient porosity to allow transfer of $0_2$ and nutrients from outside the top layer to the cells and transfer of $CO_2$ from the cells to the outside of the top layer.

11. A method according to claim 10, further comprising a partition layer disposed on at least one surface of said layered structure.

12. A method according to claim 10, wherein said cell delivery system further comprises a supply of nutrients for said cells.

13. A method according to claim 12, wherein said nutrients are selected from the group consisting of sugars, amino acids, growth factors, vitamins, hormones, cytokines and mixtures thereof.

14. A method according to claim 12, wherein said nutrients are contained within said fibers.

15. A method according to claim 10, wherein said base layer has a thickness in the range of about 20 to about 500 microns.

16. A method according to claim 15, wherein said base layer has a thickness in the range of about 50 to about 250 microns.

17. A method according to claim 10, wherein said top layer has a thickness in the range of about 1 to about 50 microns.

18. A method according to claim 17, wherein said top layer has a thickness in the range of about 5 to about 20 microns.

19. A method according to claim 1, wherein said preservation temperature is below at least about −50° C.

20. A method according to claim 19, wherein said cooling step is carried out by submerging said cell delivery system in liquid nitrogen.

21. A method according to claim 1, said cell delivery system further comprising a layered structure which comprises:
   a relatively thick base layer of the biodegradable and/or bioabsorbable fibrous matrix,
   a dispersion of cells dispersed over the surface of said base layer, and
   a top coating of a biological gel material covering said dispersion of cells and adhered to the surface of said base layer.

22. A method according to claim 21, wherein said biological gel material comprises a material selected from the group consisting of collagen, gelatin, polypeptides, proteins, hyaluronic acid and derivatives or synthetic biopolymers and their mixtures.

* * * * *

UNITED STATES PATENT AND TRADEMARK OFFICE
CERTIFICATE OF CORRECTION

PATENT NO.         : 8,021,869 B2
APPLICATION NO.    : 11/986107
DATED              : September 20, 2011
INVENTOR(S)        : Chu et al.

It is certified that error appears in the above-identified patent and that said Letters Patent is hereby corrected as shown below:

Column 1, after line 11 and before "Background of Invention", please add:

-- This invention was made with Government support under Grant No. DAAD 190010419 awarded by the Office of Army Research. The Government has certain rights in the invention. --

Signed and Sealed this
Thirty-first Day of July, 2012

David J. Kappos
*Director of the United States Patent and Trademark Office*